US009597036B2

(12) United States Patent
Aeby et al.

(10) Patent No.: US 9,597,036 B2
(45) Date of Patent: Mar. 21, 2017

(54) TRIAXIAL FIBER OPTIC FORCE SENSING CATHETER AND METHOD OF USE

(71) Applicant: St. Jude Medical International Holding S.à r.l., Luxembourg (LU)

(72) Inventors: Nicolas Aeby, Geneva (CH); Giovanni Leo, Chene Bougeries (CH)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 551 days.

(21) Appl. No.: 14/064,898

(22) Filed: Oct. 28, 2013

(65) Prior Publication Data
US 2014/0121537 A1    May 1, 2014

Related U.S. Application Data

(63) Continuation of application No. 12/352,426, filed on Jan. 12, 2009, now Pat. No. 8,567,265, which is a
(Continued)

(51) Int. Cl.
*A61B 19/00* (2006.01)
*A61B 5/00* (2006.01)
(Continued)

(52) U.S. Cl.
CPC .......... *A61B 5/6885* (2013.01); *A61B 5/0084* (2013.01); *A61B 5/0422* (2013.01);
(Continued)

(58) Field of Classification Search
CPC  A61B 18/22; A61B 18/24; G01L 1/24; G01L 1/241; G01L 1/242; G01L 1/243; G01L 1/245
(Continued)

(56) References Cited

U.S. PATENT DOCUMENTS 4,757,194 A    7/1988  Simms et al.
4,873,989 A   10/1989  Einzig et al.
(Continued)

FOREIGN PATENT DOCUMENTS

CN    103239241 A    8/2013
CN    10428471       12/2014
(Continued)

OTHER PUBLICATIONS

"Endosense achieves ISO 13485 certification", Aug. 12, 2008, 1 pg.
(Continued)

*Primary Examiner* — Ahmed Farah
(74) *Attorney, Agent, or Firm* — Dykema Gossett PLLC

(57) ABSTRACT

A fiber optic force sensing assembly for detecting forces imparted at a distal end of a catheter assembly. The structural member may include segments adjacent each other in a serial arrangement, with gaps located between adjacent segments that are bridged by flexures. Fiber optics are coupled to the structural member. In one embodiment, each fiber optic has a distal end disposed adjacent one of the gaps and oriented for emission of light onto and for collection of light reflected from a segment adjacent the gap. The optical fibers cooperate with the deformable structure to provide a change in the intensity of the reflected light, or alternatively to provide a variable gap interferometer for sensing deformation of the structural member. In another embodiment, the gaps are bridged by fiber Bragg gratings that reflect light back through the fiber optic at central wavelengths that vary with the strain imposed on the grating.

16 Claims, 11 Drawing Sheets

Related U.S. Application Data continuation-in-part of application No. 11/450,072, filed on Jun. 9, 2006, now Pat. No. 8,048,063.

(60) Provisional application No. 61/143,718, filed on Jan. 9, 2009.

(51) Int. Cl.
| | | |
|---|---|---|
| *A61B 5/042* | (2006.01) | |
| *A61B 17/3207* | (2006.01) | |
| *A61B 18/14* | (2006.01) | |
| *G01L 5/16* | (2006.01) | |
| *A61B 18/02* | (2006.01) | |

(52) U.S. Cl.
CPC .... *A61B 5/6849* (2013.01); *A61B 17/320758* (2013.01); *A61B 18/1492* (2013.01); *A61B 90/06* (2016.02); *G01L 5/166* (2013.01); *A61B 18/02* (2013.01); *A61B 2090/064* (2016.02); *A61B 2090/065* (2016.02); *A61B 2562/02* (2013.01); *A61B 2562/0266* (2013.01)

(58) Field of Classification Search
USPC ............... 606/1, 13–18; 250/227.14, 227.16; 385/12, 13; 73/862, 862.041, 862.045, 73/862.321, 862.381, 862.471, 862.621, 73/862.624, 862.636–862.641
See application file for complete search history.

(56) References Cited

U.S. PATENT DOCUMENTS

| | | | |
|---|---|---|---|
| 4,918,492 A | 4/1990 | Ferdinand et al. | |
| 4,966,597 A | 10/1990 | Cosman | |
| 4,983,034 A | 1/1991 | Spillman et al. | |
| 5,014,709 A | 5/1991 | Bjelkhagen et al. | |
| 5,018,529 A | 5/1991 | Tenerz et al. | |
| 5,065,010 A | 11/1991 | Knute et al. | |
| 5,104,392 A | 4/1992 | Kittrell et al. | |
| 5,122,137 A | 6/1992 | Lennox | |
| 5,178,153 A | 1/1993 | Einzig et al. | |
| 5,201,317 A | 4/1993 | Kanazawa et al. | |
| 5,202,939 A | 4/1993 | Belleville et al. | |
| 5,279,793 A | 1/1994 | Glass et al. | |
| 5,289,256 A | 2/1994 | Gramling | |
| 5,321,501 A | 6/1994 | Schuman et al. | |
| 5,321,510 A | 6/1994 | Childers et al. | |
| 5,348,019 A | 9/1994 | Sluss et al. | |
| 5,392,117 A | 2/1995 | Belleville et al. | |
| 5,396,887 A | 3/1995 | Imran | |
| 5,409,000 A | 4/1995 | Imran et al. | |
| 5,423,807 A | 6/1995 | Milder | |
| 5,446,546 A | 8/1995 | Breidenbach et al. | |
| 5,575,787 A | 11/1996 | Abela et al. | |
| 5,594,819 A | 1/1997 | Narendran et al. | |
| 5,633,494 A | 5/1997 | Danisch et al. | |
| 5,645,065 A | 7/1997 | Shapiro et al. | |
| 5,662,108 A | 9/1997 | Beatty et al. | |
| 5,688,267 A | 11/1997 | Panescu et al. | |
| 5,693,043 A | 12/1997 | Kittrell et al. | |
| 5,696,863 A | 12/1997 | Kleinerman et al. | |
| 5,769,847 A | 6/1998 | Panescu et al. | |
| 5,772,590 A | 6/1998 | Webster | |
| 5,782,828 A | 7/1998 | Chen et al. | |
| 5,798,521 A | 8/1998 | Froggatt | |
| 5,807,265 A | 9/1998 | Itoigawa et al. | |
| 5,833,688 A | 11/1998 | Sieben et al. | |
| 5,844,927 A | 12/1998 | Kringlebotn et al. | |
| 5,859,717 A | 1/1999 | Scobey et al. | |
| 5,904,658 A | 5/1999 | Niederauer et al. | |
| 5,906,614 A | 5/1999 | Stern et al. | |
| 5,967,978 A | 10/1999 | Littmann et al. | |
| 6,039,743 A | 3/2000 | Quiachon et al. | |
| 6,056,436 A | 5/2000 | Singh et al. | |
| 6,063,078 A | 5/2000 | Wittkampf | |
| 6,066,130 A | 5/2000 | Gregory et al. | |
| 6,088,088 A | 7/2000 | Fortenberry et al. | |
| 6,102,926 A | 8/2000 | Tartaglia et al. | |
| 6,113,590 A | 9/2000 | Fischer et al. | |
| 6,113,593 A | 9/2000 | Tu et al. | |
| 6,120,476 A | 9/2000 | Fung et al. | |
| 6,120,520 A | 9/2000 | Saadat et al. | |
| 6,129,667 A | 10/2000 | Dumoulin et al. | |
| 6,133,593 A | 10/2000 | Boos et al. | |
| 6,134,003 A | 10/2000 | Fujimoto et al. | |
| 6,171,275 B1 | 1/2001 | Webster | |
| 6,173,091 B1 | 1/2001 | Reich et al. | |
| 6,175,669 B1 | 1/2001 | Colston et al. | |
| 6,197,023 B1 | 3/2001 | Muntermann et al. | |
| 6,210,346 B1 | 4/2001 | Hall et al. | |
| 6,217,574 B1 | 4/2001 | Webster et al. | |
| 6,226,542 B1 | 5/2001 | Reisfeld et al. | |
| 6,226,551 B1 | 5/2001 | Zhu et al. | |
| 6,246,898 B1 | 6/2001 | Vesely et al. | |
| 6,256,090 B1 | 7/2001 | Chen et al. | |
| 6,262,822 B1 | 7/2001 | Obhi et al. | |
| 6,266,542 B1 | 7/2001 | Stern et al. | |
| 6,266,551 B1 | 7/2001 | Osadchy et al. | |
| 6,272,371 B1 | 8/2001 | Shlomo et al. | |
| 6,276,215 B1 | 8/2001 | Berg et al. | |
| 6,310,990 B1 | 10/2001 | Bellemore et al. | |
| 6,324,918 B1 | 12/2001 | Gitis et al. | |
| 6,370,412 B1 | 4/2002 | Armoundas et al. | |
| 6,398,778 B1 | 6/2002 | Gu et al. | |
| 6,425,894 B1 | 7/2002 | Brucker et al. | |
| 6,451,009 B1 | 9/2002 | Dasilva et al. | |
| 6,458,123 B1 | 10/2002 | Brucker et al. | |
| 6,466,811 B1 | 10/2002 | Hassett et al. | |
| 6,470,205 B2 | 10/2002 | Bosselmann et al. | |
| 6,470,286 B1 | 10/2002 | Watts et al. | |
| 6,471,710 B1 | 10/2002 | Bucholtz | |
| 6,546,271 B1 | 4/2003 | Reisfeld et al. | |
| 6,547,780 B1 | 4/2003 | Sinofsky et al. | |
| 6,558,378 B2 | 5/2003 | Sherman et al. | |
| 6,563,970 B1 | 5/2003 | Bohnert et al. | |
| 6,572,804 B2 | 6/2003 | Randall et al. | |
| 6,602,242 B1 | 8/2003 | Fung et al. | |
| 6,660,001 B2 | 12/2003 | Gregory et al. | |
| 6,674,928 B2 | 1/2004 | Johnson et al. | |
| 6,695,808 B2 | 2/2004 | Tom | |
| 6,701,931 B2 | 3/2004 | Sliwa et al. | |
| 6,852,109 B2 | 2/2005 | Winston et al. | |
| 6,868,195 B2 | 3/2005 | Fujita et al. | |
| 6,898,338 B2 | 5/2005 | Kersey et al. | |
| 6,915,048 B2 | 7/2005 | Kersey et al. | |
| 6,947,637 B2 | 9/2005 | Smith et al. | |
| 6,955,675 B2 | 10/2005 | Jain et al. | |
| 6,986,769 B2 | 1/2006 | Nelson et al. | |
| 7,050,662 B2 | 5/2006 | Behrmann et al. | |
| 7,114,938 B2 | 10/2006 | Chou et al. | |
| 7,173,713 B2 | 2/2007 | Xu et al. | |
| 7,241,986 B2 | 7/2007 | Wang et al. | |
| 7,460,964 B2 | 12/2008 | Mizota et al. | |
| 7,466,879 B2 * | 12/2008 | Tjin | G01D 5/35303 385/12 |
| 7,491,957 B2 | 2/2009 | Kitamura et al. | |
| 8,048,063 B2 * | 11/2011 | Aeby | A61B 5/042 385/13 |
| 8,075,498 B2 | 12/2011 | Leo et al. | |
| 8,157,789 B2 | 4/2012 | Leo et al. | |
| 8,182,433 B2 | 5/2012 | Leo et al. | |
| 8,435,232 B2 | 5/2013 | Leo et al. | |
| 8,567,265 B2 * | 10/2013 | Aeby | A61B 5/0084 606/1 |
| 8,622,935 B1 * | 1/2014 | Leo | A61B 5/6843 600/585 |
| 8,894,589 B2 | 11/2014 | Leo et al. | |
| 8,932,288 B2 | 1/2015 | Leo et al. | |
| 8,961,436 B2 | 2/2015 | Leo et al. | |
| 2001/0021843 A1 | 9/2001 | Bosselmann et al. | |
| 2002/0041722 A1 | 4/2002 | Johnson et al. | |
| 2002/0041723 A1 | 4/2002 | Ronnekleiv et al. | |
| 2002/0057859 A1 | 5/2002 | Walter et al. | |

(56) References Cited

U.S. PATENT DOCUMENTS

| | | | |
|---|---|---|---|
| 2002/0072680 | A1 | 6/2002 | Schock et al. |
| 2004/0082844 | A1 | 4/2004 | Vardi et al. |
| 2004/0165810 | A1 | 8/2004 | Fujita et al. |
| 2004/0206365 | A1 | 10/2004 | Knowlton et al. |
| 2004/0243119 | A1 | 12/2004 | Lane et al. |
| 2005/0062979 | A1 | 3/2005 | Zhu et al. |
| 2005/0213870 | A1 | 9/2005 | Kersey et al. |
| 2006/0013523 | A1 | 1/2006 | Childers et al. |
| 2006/0045408 | A1 | 3/2006 | Jones et al. |
| 2006/0100610 | A1 | 5/2006 | Wallace et al. |
| 2006/0133715 | A1 | 6/2006 | Belleville et al. |
| 2006/0200049 | A1 | 9/2006 | Leo et al. |
| 2006/0263002 | A1 | 11/2006 | Pocha et al. |
| 2007/0014490 | A1 | 1/2007 | Silverbrook et al. |
| 2007/0041019 | A1 | 2/2007 | Schmidt et al. |
| 2007/0043338 | A1 | 2/2007 | Moll et al. |
| 2007/0060847 | A1* | 3/2007 | Leo .................. A61B 5/0084 600/587 |
| 2007/0065077 | A1 | 3/2007 | Childers et al. |
| 2007/0151390 | A1 | 7/2007 | Blumenkranz et al. |
| 2007/0151391 | A1 | 7/2007 | Larkin et al. |
| 2007/0156019 | A1 | 7/2007 | Larkin et al. |
| 2007/0265503 | A1 | 11/2007 | Schlesinger et al. |
| 2008/0009750 | A1 | 1/2008 | Leo et al. |
| 2008/0294144 | A1 | 11/2008 | Leo et al. |
| 2009/0138007 | A1 | 5/2009 | Govari et al. |
| 2009/0177095 | A1 | 7/2009 | Aeby et al. |
| 2009/0287092 | A1* | 11/2009 | Leo .................. A61B 5/00 600/474 |
| 2009/0306650 | A1 | 12/2009 | Govari et al. |
| 2010/0063478 | A1 | 3/2010 | Selkee et al. |
| 2010/0087835 | A1 | 4/2010 | Blumenkranz et al. |
| 2010/0094163 | A1 | 4/2010 | Deladi et al. |
| 2010/0328675 | A1 | 12/2010 | Bertholds et al. |
| 2011/0087112 | A1 | 4/2011 | Leo et al. |
| 2012/0078138 | A1 | 3/2012 | Leo et al. |
| 2012/0179068 | A1 | 7/2012 | Leo et al. |
| 2012/0265102 | A1 | 10/2012 | Leo et al. |

FOREIGN PATENT DOCUMENTS

| | | |
|---|---|---|
| CN | 104244808 A | 12/2014 |
| DE | 3020785 A1 | 12/1981 |
| DE | 3828550 A1 | 3/1990 |
| EP | 0281405 | 9/1988 |
| EP | 0934728 | 8/1999 |
| EP | 1909650 A2 | 4/2008 |
| EP | 2047797 B1 | 4/2014 |
| JP | 09297076 A | 11/1997 |
| JP | 10137200 A | 5/1998 |
| JP | 20000227367 | 8/2000 |
| JP | 2004251779 A | 9/2004 |
| WO | 9729678 A2 | 8/1997 |
| WO | 9732182 | 9/1997 |
| WO | 9738637 A1 | 10/1997 |
| WO | 9819044 A1 | 5/1998 |
| WO | 9945994 A1 | 9/1999 |
| WO | 0133165 A1 | 5/2001 |
| WO | 0174252 A2 | 10/2001 |
| WO | 0219898 A2 | 3/2002 |
| WO | 0219903 A1 | 3/2002 |
| WO | 0223148 A1 | 3/2002 |
| WO | 0247751 A2 | 6/2002 |
| WO | 2004002303 A1 | 1/2004 |
| WO | 2005059510 A1 | 6/2005 |
| WO | 2005059510 A2 | 6/2005 |
| WO | 2006092707 A1 | 9/2006 |
| WO | 2007015139 A3 | 4/2007 |
| WO | 2007050960 A2 | 5/2007 |
| WO | 2007111737 A2 | 10/2007 |
| WO | 2008000246 A2 | 1/2008 |
| WO | 2008003307 A2 | 1/2008 |
| WO | 2008045958 | 4/2008 |
| WO | 2009114955 A1 | 9/2009 |

OTHER PUBLICATIONS

"Endosense launches TOCCATA clinical study", Multi-center European Safety Study on Groundbreaking Technology for the Treatment of Atrial Arrhythmias, Oct. 7, 2008, 1 pg.

"Endosense receives CE mark for Tacticath force-sensing ablation catheter", May 4, 2009, 1 pg.

"Endosense unveils five groundbreaking abstracts on contact force measurement for catheter ablation", May 13, 2008, 1 pg.

"Hansen Medical product brochure", Artisan extend Control Catheter, Unknown publication date, 2 pgs.

"Hansen Medical product brochure", Sensie Robotic Catheter System, Unknown publication date, 7 pgs.

"IntelliSense Fine Force Technology", Hansen Medical (website) http://www.hansenmedical.com/products/intellisense.aspx, Sep. 22, 2009, 1 pg.

"Precision Photonics Corporation", Basic Physics and Design of Etalons, 2003, 1-5.

"The Unique Force Sensor Ablation Catheter", www.endosense.com/site/product.htm, Mar. 14, 2007, 1 pg.

Barb, et al., "Versatile, High-Speed Force Transducer Using a Laser Diode Beam as an Optical Lever", Journal of Applied Physiology, vol. 88, No. 1. 2000, 308-314.

Barrett, et al., "Extrinsic Fabry-Perot Interometer for Measuring the Stiffness of Ciliary Bundles of Hair Cells", IEEE Transactions on Biomedical Engineering, vol. 46, No. 3, Mar. 1999, 331-339.

Brown, "Development of Biollouin Scattering Based Distributed Fiber-Optic Strain Sensor", The University of New Brunswick, 2001. 2 pgs.

Calkins, et al., "HRS/EHRA/ECAS Expert Consensus Statement on Catheter and Surgical Ablation of Atrial Fibrillation: Recommendations of Personnel, Policy, Procedures and Follow-up", Eurospace (2007) 9, 335-379.

Cappato, et al., "Worldwide Suvey on the Mehods, Efficacy, and Safety of Catheter Ablation for Human Atrial Fibrillation", Journal of the American Heart Association, 2005, 7 pgs.

Del Villar, et al., "Optimization of Sensitivity in Long Period Fiber Gratings with Overlay Deposition", Optic Express, vol. 13, No. 1, Jan. 10, 2005, 56-69.

Dickmann, "Experiment 03, Fabry Perot Resonator", 2003, 1-19.

Dupont, "DuPont Zenite LCP liquid crystal polymer resin", Product and Property Guide, K-15415, May 2006. 35 pgs.

Erdemir, et al., "Fiberoptic Measurement of Tendon Forces is Influenced by Skin Movement Artifact", Journal of Biomechanics, vol. 36, No. 3, 449-455, Mar. 2003.

European Office Action, EP Application No. 067951863, Aug. 9, 2011, 5 pgs.

European Office Action, EP Application No. 11158967.7, Aug. 10, 2011, 8 pgs.

European Office Action, "European Office Action for EP Application No. 06710474.5", Feb. 16, 2009, 3 pgs.

European Office Action, "European Office Action for Application No. 06710474.5", Aug. 24, 2009, 4 pgs.

European Office Action, "European Office Action for EP Application No. 09746251.9", dated Jan. 24, 2012, 4 pgs.

Fearn, et al., "An Optical Fiber Transducer for Single Myofibril Force Measurement", IEEE Transactions on Biomedical Engineering, vol. 40, No. 11, 1993, 1127-1132.

Fernandez, et al., "Multi-component force sensor based on multiplexed fibre Bragg grating strain sensors", Meas. Sci. Technol. 12, 2001, 1-4.

FISO, "FOS-N Strain Sensor", FISO Technologies Inc. Canada, 2006, 2 pgs.

FISO Technologies, "Technical Note, Principle of Fiber-Optic Sensors", Unknown Publication Date, 2 pgs.

Fuster, et al., "ACC/AHA/ESC 2006 Guidelines for the Management of Patients with Atrial Fibrillation", Circulation Journal of the American Heart Association, 2006, e319-e321.

Hasin, et al., "Miniature Force Transducer for Myocardial Stimulation and Local Tension Measurements", IEEE Transactions on Biomedical Engineering, vol. BME-26, No. 2, Feb. 1979, 104-105.

(56) References Cited

OTHER PUBLICATIONS

Inaudi, "Application of optical fiber sensor in civil structural monitoring", Proceedings of the SPIE—The International Society for Optical Engineering SPIE-INT. Soc. Opt. Eng USA, vol. 4328, 2001, 1-10.

International Search Report, PCT Application No. PCT/IB2008/002675, 1 pg.

International Search Report, International Application No. PCT/IB2010/000021, May 27, 2010.

Shah, et al., "Evaluation of a New Catheter Sensor for Real-Time Measurement of Tissue Contact", Heart Rhythm Society, vol. 3, Issue 5 (Supplement), S75-576, AB36-6, May 2006, 1 pg.

International Search Report, "ISR and Written Opinion for International Application No. PCT/IB2009/051967", Mar. 16. 2010, 4 pgs.

Komi et al., "Optic Fibre as a Transducer of Tendomuscular Forces", European Journal of Applied Physiology and Occupational Physiology, Vo. 72, No. 3, 1996, 248-280.

Lo, "Using in-fiber Bragg-grating sensors for measuring axial strain and temperatures simultaneously on surface of structures", Optical Engineering, vol. 37, Aug. 1998, 2272-2276.

Luna Innovations, "EFPI Techniques for Strain and Displacement Sensing", Rec. C, Aug. 1999, 6 pgs.

Luna Innovations, "Fiber Optic Bragg Grating Sensor", www.lunainnovations.com/products/shape.asp, Aug. 2005, 18 pgs.

Meller, "Extrinsic Fabry-Perot Interferometer System Using Wavelength Modulated Source", Dec, 1996, 57 pgs.

Natale, et al., "Venice Chart International Consensus Document on Atrial Fibrillation Ablation", Journal of Cardiovascular Electrophysiology, vol. 18, No. 5, 2007, 560-580.

Notification, "Notificaton of the First Chinese Office Acion for Chinese Application No. 20068007106.8", May 8, 2009, 4 pgs.

NTT Innovative Technology, "Fiber-Optic Strain-Monitoring Technology: BOTDR (Brillouin Optical Time Domain Reflectometer)", http://www.ntt-tech.jp/technology/C316.html. 2 pgs. Jul. 18, 2005.

Paris-Seely, et al., "A Compliance-Independent Pressure Transducer for Biomedical Device-Tissue Interfacesm", Biomedical Instrumentation & Technology, vol. 34, No. 6, Nov.-Dec. 2000, 423-31.

Park, et al., "Force Sensing Robot Fingers using embedded Fiber Bragg Grating Sensors and Shap Deposition Manugacturing", Center for Design Research, Stanford University, Intelligent Fiber Optic Systems Corporation, Santa Clara, California. 7 pgs. Unknown Publication Date.

Peirs, et al., "A micro optical for force feedback during minimally invasive robotic surgery", Sensors and Actuators A 115: 2004, 447-455.

Peirs, et al., "Design of an Optical Force Sensor for Force Feeback during Minimally Invasive Robotic Surgery", Katholieke Universiteit Leuven, Dept. of Mechanical Engineering, Celestijnenlaan 300B, 3001 Leuven, Belgium, Unknown Publication Date, 4 pgs.

Rao, "Recent progress in applications of in-fibre Bragg grating sensors", Optics and Lasers in Engineering Elseiver UK, vol. 31, No. 4, Apr. 1999, 297-324.

Schmidt, et al., "Fiber-Optic Extrinsic Fabry-Perot Interoferometer Strain Sensor with <50 pm Displacement Resolution Using Three-Wavelength Digital Phase Demodulation", Optic Express, vol. 8, No. 8, Apr. 9, 2001, 475-480.

Sensei X Robotic, "Sensei X Robotic Catheter System for Electrophysiology Procedures", MedGadget, Sep. 18, 2009. 4 pgs.

Yokoyama, et al. "Novel Radiofrequency Ablation Catheter with Contact Force Sensor Predicts Lesion Size and Incidence of Steam Pop in Canine Model", Heart Rhythm Society, vol. 4, Issue 5 (Supplement), S340-S341, P05-106. 1 pg. May 2007.

Zhang, et al. "On SDM/WDM FBG Sensor Net for Shape Detection of Endoscope".Proceedings of the IEEE, International Conference on Mechatronics and Automation, Niagra Falls, Canada. Jul. 2005. pp. 1986-1991.

Xiao, et al. "Fiber optic pressure sensor with self-compensation capability for harsh environment applications". Optical Engineering 44(5), 054-403, XP-002527158. May 2005. 10 pgs.

Van Uffelen, et al. "Anchoring points for fibre optic strain sensors". Optical Techniques for Smart Structures and Structural Monitoring. 1 pg. Feb. 17, 1997.

\* cited by examiner

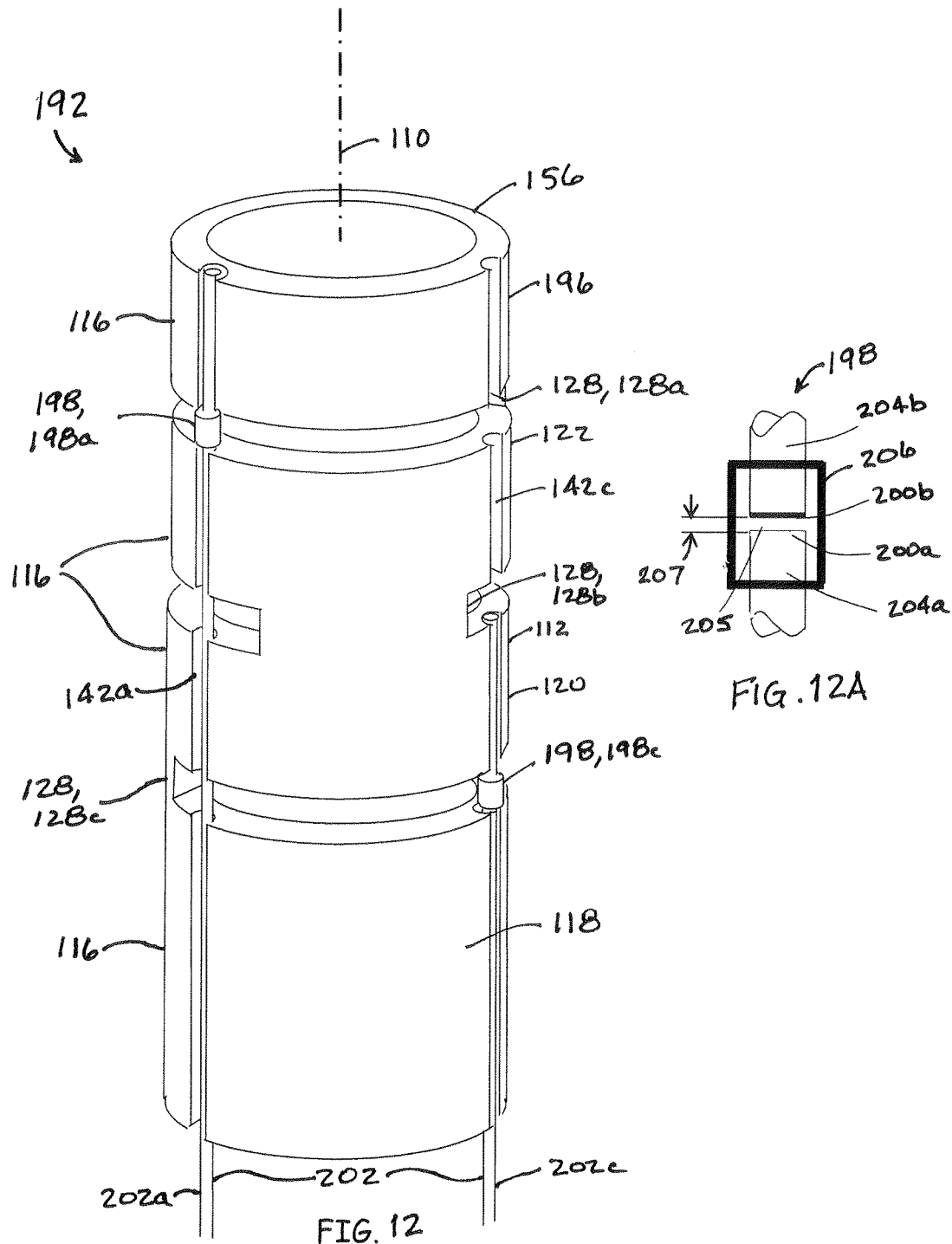

TRIAXIAL FIBER OPTIC FORCE SENSING CATHETER AND METHOD OF USE

RELATED APPLICATIONS

This application is a continuation of U.S. patent application Ser. No. 12/352,426, filed Jan. 12, 2009, now U.S. Pat. No. 8,567,265, which is: (1) a continuation-in-part of U.S. patent application Ser. No. 11/450,072, filed Jun. 9, 2006, now U.S. Pat. No. 8,048,063; and (2) claims benefit of the filing date of U.S. Provisional Patent Application No. 61/143,718, filed Jan. 9, 2009. The disclosures of each of these applications are hereby incorporated by reference in their entireties.

FIELD OF THE INVENTION

The disclosed invention relates generally to force sensing devices capable of resolving the magnitude and direction of a force vector. More specifically, the invention relates to a force sensing tip to aid in the positioning of catheters used in humans or animals, or for serving as feedback elements in robotic surgical systems.

BACKGROUND

For many years, exploration and treatment of various organs or vessels has been possible using catheter-based diagnostic and treatment systems. Such catheters are introduced through a vessel leading to the cavity of the organ to be explored or treated or alternatively may be introduced directly through an incision made in the wall of the organ. In this manner, the patient avoids the trauma and extended recuperation times typically associated with open surgical procedures.

To provide effective diagnosis or therapy, it is frequently necessary to first map the zone to be treated with great precision. Such mapping may be performed, for example, when it is desired to selectively ablate current pathways within a heart to treat atrial fibrillation. Often, the mapping procedure is complicated by difficulties in locating the zone(s) to be treated due to periodic movement of the heart throughout the cardiac cycle.

Previously-known systems for mapping the interior of a vessel or organ are described, for example, in U.S. Pat. Nos. 6,546,271 and 6,226,542. The catheters described in those patents employ electromagnetic, electrical, magnetic or acoustic sensors to map the position of a distal end of the catheter in space and then construct a three-dimensional visualization of the vessel or organ interior.

One drawback of such previously known mapping systems is that they rely on manual feedback of the catheter and/or impedance measurements to determine when the catheter is properly positioned in the vessel or organ. Those systems do not measure contact forces with the vessel or organ wall or detect contact forces applied by the catheter against the organ or vessel wall that may modify the true wall location. Instead, previously known mapping methods are time-consuming, dependent upon the skill of the clinician, and cannot compensate for artifacts created by excessive contact forces.

It therefore would be desirable to provide apparatus and methods for detecting and monitoring contact forces between a mapping catheter and the wall of the organ or vessel to permit faster and more accurate mapping. It also would be desirable to provide apparatus and methods that permit the process to be automated.

Once the topography of the vessel or organ is mapped, either the same or a different catheter may be employed to effect treatment. Depending upon the specific treatment to be applied to the vessel or organ, the catheter may comprise any of a number of end effectors, such as but not limited to RF ablation electrodes, rotary or scissor action cutting heads, laser ablation system, injection or sewing needles, fluid conveyance systems, forceps, manipulators, mapping electrodes, endoscopic vision systems and therapeutic delivery systems such as genetic impregnation devices. Exemplary systems are described, for example, in U.S. Pat. Nos. 6,120,520, 6,102,926, 5,575,787, 5,409,000 and 5,423,807.

The effectiveness of such end effectors often depends on having the end effector in contact with the tissue of the wall of the organ or vessel. Many previously-known treatment systems include expandable baskets or hooks that stabilize the distal extremity of the catheter in contact with the tissue. Such arrangements, however, may be inherently imprecise due to the motion of the organ or vessel. Moreover, the previously-known systems do not provide the ability to sense the load applied to the distal extremity of the catheter by movement of the tissue wall.

For example, in the case of a cardiac ablation system, at one extreme the creation of a gap between the end effector of the treatment system and the tissue wall may render the treatment ineffective, and inadequately ablate the tissue zone. At the other extreme, if the end effector of the catheter contacts the tissue wall with excessive force, it may inadvertently puncture the tissue, resulting in cardiac tamponade.

In view of the foregoing, it would be desirable to provide a catheter-based diagnostic or treatment system that permits sensing of the load applied to the distal extremity of the catheter, including periodic loads arising from movement of the organ or tissue. It further would be desirable to have a load sensing system coupled to control operation of the end effector, so that the end effector is operated, either manually or automatically, only when the contact force is detected to fall within a predetermined range.

U.S. Pat. No. 6,695,808 proposes several solutions to measure the force vector arising from contact with the tissue surface, including mechanical, capacitive, inductive and resistive pressure sensing devices. One drawback of such devices, however, is that they are relatively complex and must be sealed to prevent blood or other liquids from disturbing the measurements. In addition, such load sensing devices may result in an increase in the insertion profile of the distal extremity of the catheter. Still further, sensors of the types described in that patent may be subject to electromagnetic interference.

One previously-known solution for dealing with potential electromagnetic interference in the medical environment is to use light-based systems rather than electrical measurement systems. One such light-based system is described in U.S. Pat. No. 6,470,205 to Bosselman which describes a robotic system for performing surgery comprising a series of rigid links coupled by articulated joints. A plurality of Bragg gratings are disposed at the articulated joints so that the bend angle of each joint may be determined optically, for example, by measuring the change in the wavelength of light reflected by the Bragg gratings using an interferometer.

International Publication No. WO 01/33165 to Bucholtz describes an alternative spatial orientation system wherein wavelength changes measured in a triad of optical fiber strain sensors are used to compute the spatial orientation of a catheter or other medical instrument. Although Bucholtz discloses that the strain sensors may be encased within a deformable sheath, as is also described in Bosselman, calculation of the bend angles is not described as requiring characterization of the material properties of the deformable sheath.

Accordingly, it would be desirable to provide diagnostic and treatment apparatus, such as a catheter or guide wire, that permits sensing of loads applied to a distal extremity of the apparatus, but which do not substantially increase the insertion profile of the apparatus. It is further desirable to provide diagnostic and treatment apparatus, such as a catheter and guide wire, that permits computation of forces applied to a distal extremity of the apparatus, and which are substantially immune to electromagnetic interference.

Recent advances in catheter technology have included the use of fiber optic force sensors to detect the reactive force at the distal extremity of an end effector when placed in contact with the interior wall of a vessel or organ. For example, an article by J. Peirs et al., entitled "Design of an Optical Force Sensor for Force Feedback during Minimally Invasive Robotic Surgery," published by Katholieke Universiteit Leuven, Belgium, describes a tri-axial force sensor for use generating force feedback systems in a robotic surgery system. The apparatus includes a plurality of optical fibers that direct light onto a mirrored surface disposed adjacent to a distal tip of the device. The intensity of the light reflected from the mirrored surface is measured and may be correlated to the force required to impose a predetermined amount of flexure to the distal tip. The article describes a flexible and compact structure that may be used to produce variations in light intensity responsive to contact forces that deform the structure.

International Publication No. WO 2007/015139 to Leo, et al. (Leo), discloses a device and method for resolving a force vector (magnitude and direction) applied to the distal end of a catheter. Leo discloses the use of fiber optic strain elements in a catheter that maintains essentially the same profile as with catheters that do not sense touching forces and is substantially immune to electromagnetic interference. United States Patent Application Publication No. 2007/0060847 to Leo et al. discloses a force sensing catheter system that utilizes the deformation of fiber Bragg grating strain sensors to infer the force incident upon the tip of the catheter. United States Patent Application Publication No. 2008/0294144 to Leo et al. discloses a fiber optic touch sensing catheter that utilizes an interferometric principle to detect structural deformations of a strain sensing assembly to infer forces. The above mentioned Publications to Leo et al. are assigned to the assignee of the present application, and are hereby incorporated by reference in their entirety except for explicit definitions contained therein.

Existing fiber optic strain sensing catheters are typically limited to resolving forces to within approximately ±1-gm of force. In addition, the tri-axial force sensors tend to involve complex machining and fabrication to achieve the desired isolation effect. A fiber optic touch sensing catheter having greater sensitivity (higher resolution) and that is relatively easy to fabricate would be welcome.

SUMMARY OF THE INVENTION

Various embodiments of the invention include a structural member that improves the sensitivity of the force resolution over existing fiber optic strain sensing catheters by up to an order of magnitude. Some embodiments are further characterized as having a reduced profile over existing devices.

Structurally, the flexures of the various embodiments of the present invention include a cross-section having a stiffness (area moment of inertia) about a first axis that is on the order of 20 times less than the stiffness of a second axis that is orthogonal to the first axis. The relatively small stiffness about the first axis causes the flexure to bend preferentially due to moments about the first axis while bending about the second, orthogonal axis is minimal, thereby transferring the torsional forces about the second orthogonal axis onto other portions of the structural member. In this way, the flexures enable isolation of moments and moment forces about the first axis.

In various embodiments, a structural member defines a longitudinal axis and includes a plurality of segments that are adjacent each other in a serial arrangement along the longitudinal axis. Adjacent segments may define a gap therebetween, each gap being bridged by a flexure. A plurality of fiber optics operatively coupled with the structural member. The flexure may define a cross-section on a plane orthogonal to the longitudinal axis, the cross-section defining an area centroid, and a first inertial axis and a second inertial axis may be defined as passing through the area centroid. The second inertial axis may be normal to the first inertial axis and intersect the longitudinal axis of the structural member. The area moment of inertia about the second inertial axis may be at least ten times greater than the area moment of inertia about the first inertial axis.

Certain embodiments of the invention include a flexible elongated body having a proximal end and a distal extremity. A fiber optic force sensing assembly may be disposed within the flexible elongated body proximate the distal extremity, the fiber optic force sensing assembly comprising a structural member having an outer surface and defining a longitudinal axis. The structural member may also include a plurality of segments that are adjacent each other in a serial arrangement along the longitudinal axis, the segments being bridged by flexures located between adjacent of the segments. Each of the flexures may define a portion of the outer surface of the structural member. The plurality of segments may further define a plurality of gaps, each of the plurality of gaps being located between adjacent of the plurality of segments.

A plurality of fiber optics may be disposed on the structural member, each of the plurality of fiber optics having a distal end disposed adjacent one of the plurality of gaps and oriented for emission of light onto and for collection of light reflected from the segment adjacent the one of the plurality of gaps. The distance between the distal end of the fiber optic and the segment adjacent the one of the plurality of gaps has a dimension that varies in response to a degree of deformation of the structural member when a contact force is imposed on the structural member.

The distal end of said fiber optic and said segment adjacent said one of said plurality of gaps may define an interferometric resonator for inference of the distance of deflection.

BRIEF DESCRIPTION OF THE DRAWINGS

FIG. 12 is an enlarged perspective view of a fiber optic force sensing assembly that utilizes a Fabry-Perot strain sensor in an embodiment of the invention;

FIG. 12A is a sectional view of a Fabry-Perot strain sensor of FIG. 12;

DETAILED DESCRIPTION

Figure 1:
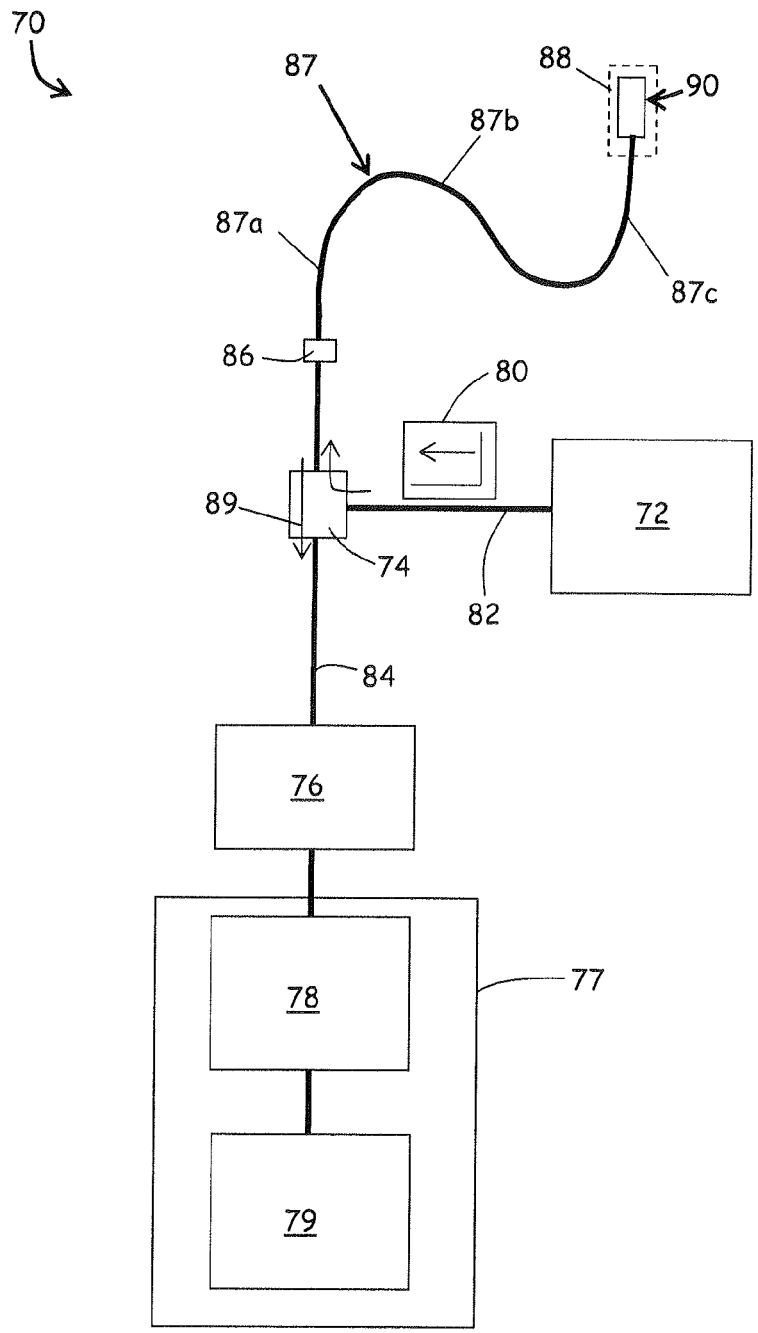
FIG. 1 is a block diagram of a strain sensing system in an embodiment of the invention.

Referring to FIG. 1, an embodiment of a strain sensing system 70 is depicted in accordance with the invention. The strain sensing system 70 may comprise an electromagnetic source 72, a coupler 74, a receiver 76, an operator console 77 operatively coupled with a microprocessor 78 and a storage device 79. The electromagnetic source 72 outputs a transmitted radiation 80 of electromagnetic radiation that is substantially steady state in nature, such as a laser or a broadband light source. A transmission line 82 such as a fiber optic cable carries the transmitted radiation 80 to the coupler 74, which directs the transmitted radiation 80 through a transmitting/receiving line 84 and through a fiber optic element 83 (FIG. 1A) contained within a flexible, elongate catheter assembly 87 to a fiber optic strain sensing element 90. The fiber optic element 83 of the catheter assembly 87 and transmitting/receiving line 84 may be coupled through a connector 86 as depicted in FIG. 1.

The catheter assembly 87 may have a width and a length suitable for insertion into a bodily vessel or organ. In one embodiment, the catheter assembly 87 comprises a proximal portion 87a, a middle portion 86b and a distal portion 87c. The distal portion 87c may include an end effector 88 which may house the fiber optic strain sensing element 90. The catheter assembly may be of a hollow construction (i.e. having a lumen) or of a non-hollow construction (i.e. no lumen), depending on the application.

Figure 1A:
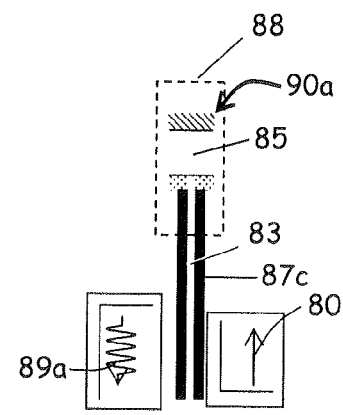
FIG. 1A is a schematic depiction of an interferometric fiber optic sensor in for use in an embodiment of the invention.
Figure 10:
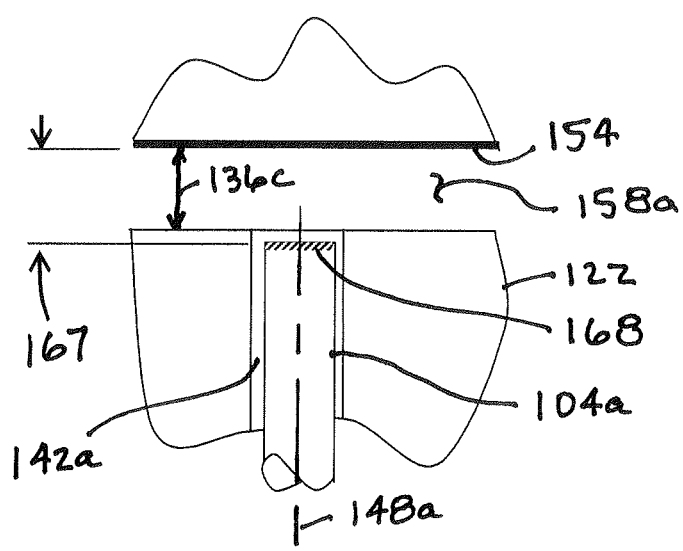
FIG. 10 is a partial enlarged view of the fiber optic force sensing assembly of FIG. 3.

Referring to FIG. 1A, an interferometric fiber optic strain sensor 90a is depicted as the fiber optic strain sensing element 90 in an embodiment of the invention. In this embodiment, the transmitted radiation 80 enters an interferometric gap 85 within the interferometric fiber optic strain sensor 90a. A portion of the radiation that enters the interferometric gap 85 is returned to the fiber optic cable of the catheter assembly 87 as a modulated waveform 89a. The various components of the interferometric fiber optic strain sensor 90a may comprise a structure that is integral with the fiber optic element 83 (e.g., FIG. 12A). Alternatively, the fiber optic element 83 may cooperate with the structure to which it is mounted to form the interferometric gap 85 (e.g., FIG. 10).

Figure 1B:
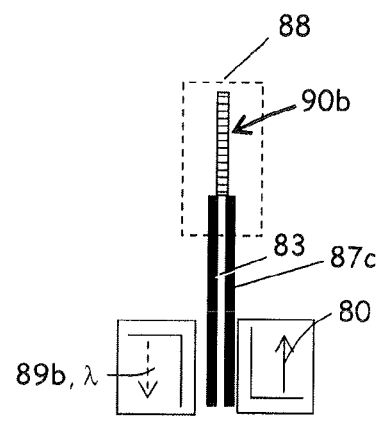
FIG. 1B is a schematic depiction of a fiber Bragg grating optical strain sensor in for use in an embodiment of the invention.

Referring to FIG. 1B, a fiber Bragg grating strain sensor 90b is depicted as the fiber optic strain sensing element 90 in an embodiment of the invention. In this embodiment, the transmitted radiation 80 enters a fiber Bragg grating 91, the gratings of which are typically integral with the fiber optic element 83 and reflect only a portion 89b of the transmitted radiation 80 about a central wavelength $\lambda$. The central wavelength $\lambda$ at which the portion 89b is reflected is a function of the spacing between the gratings of the fiber Bragg grating. Therefore, the central wavelength $\lambda$ is indicative of the strain on the fiber Bragg grating strain sensor 90b relative to some reference state.

The reflected radiation 89, be it the modulated waveform 89a or the reflected portion 89b, is transmitted back through the transmitting/receiving line 84 to the receiver 76. The strain sensing system 70 may interrogate the fiber optic strain sensing element 90 at an exemplary and non-limiting rate of 10-Hz. The receiver 76 is selected to correspond with the type of strain sensing element 90 utilized. That is, the receiver in the depicted embodiments is selected to either detect the frequency of the modulated waveform 89a for use with the interferometric fiber optic strain sensor 90a, or to resolve the central wavelength of the reflected portion 89b for use with fiber Bragg grating strain sensor 90b. The receiver 76 manipulates and/or converts the incoming reflected radiation 89 into digital signals for processing by the microprocessor 78.

Figure 2:
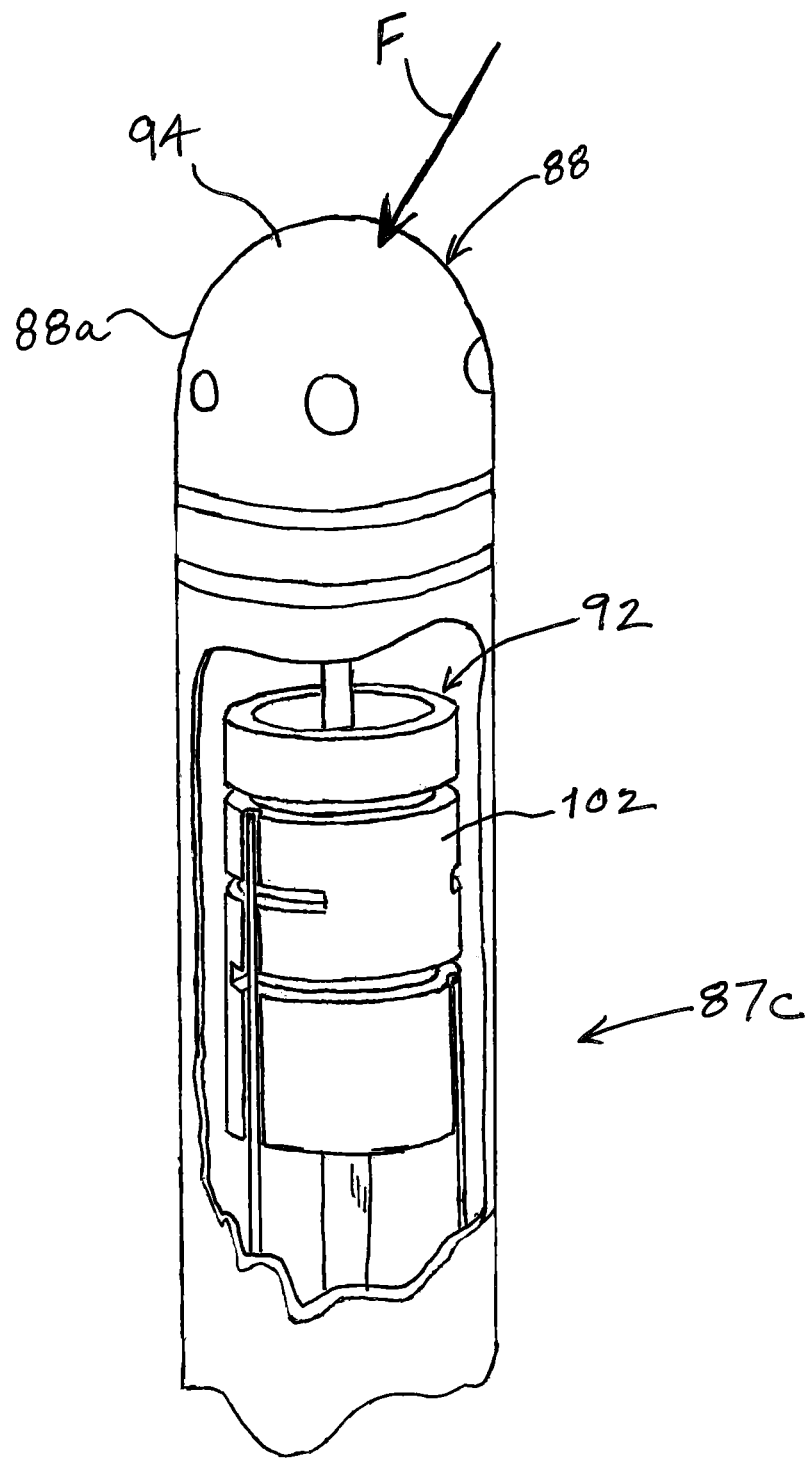
FIG. 2 is a partial cutaway view of a distal portion of a catheter assembly having a fiber optic force sensing assembly in an embodiment of the invention.
Figure 3:
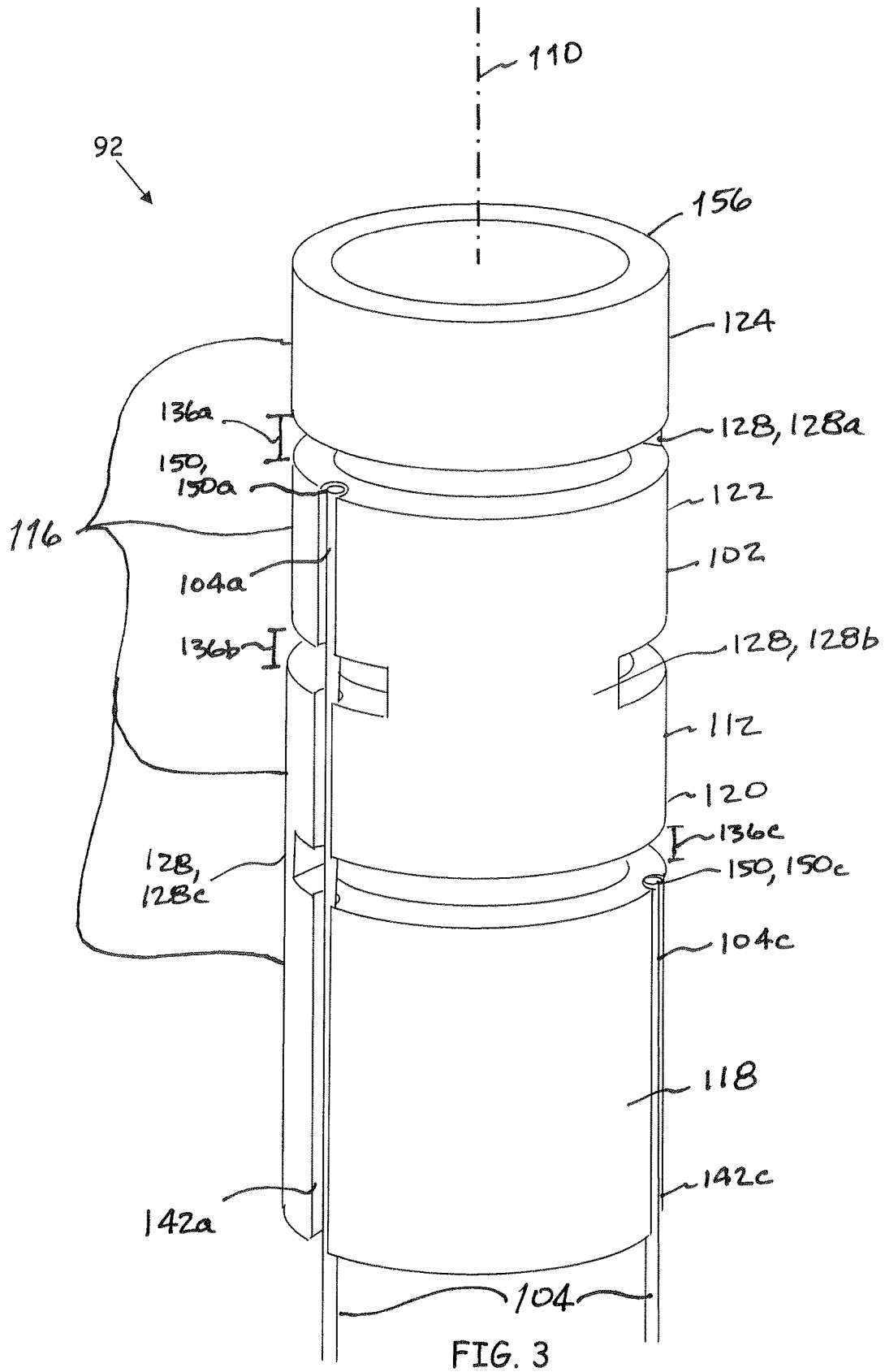
FIG. 3 is an enlarged perspective view of a fiber optic force sensing assembly that utilizes an intensity or an interferometric measurement in an embodiment of the invention.
Figure 4:
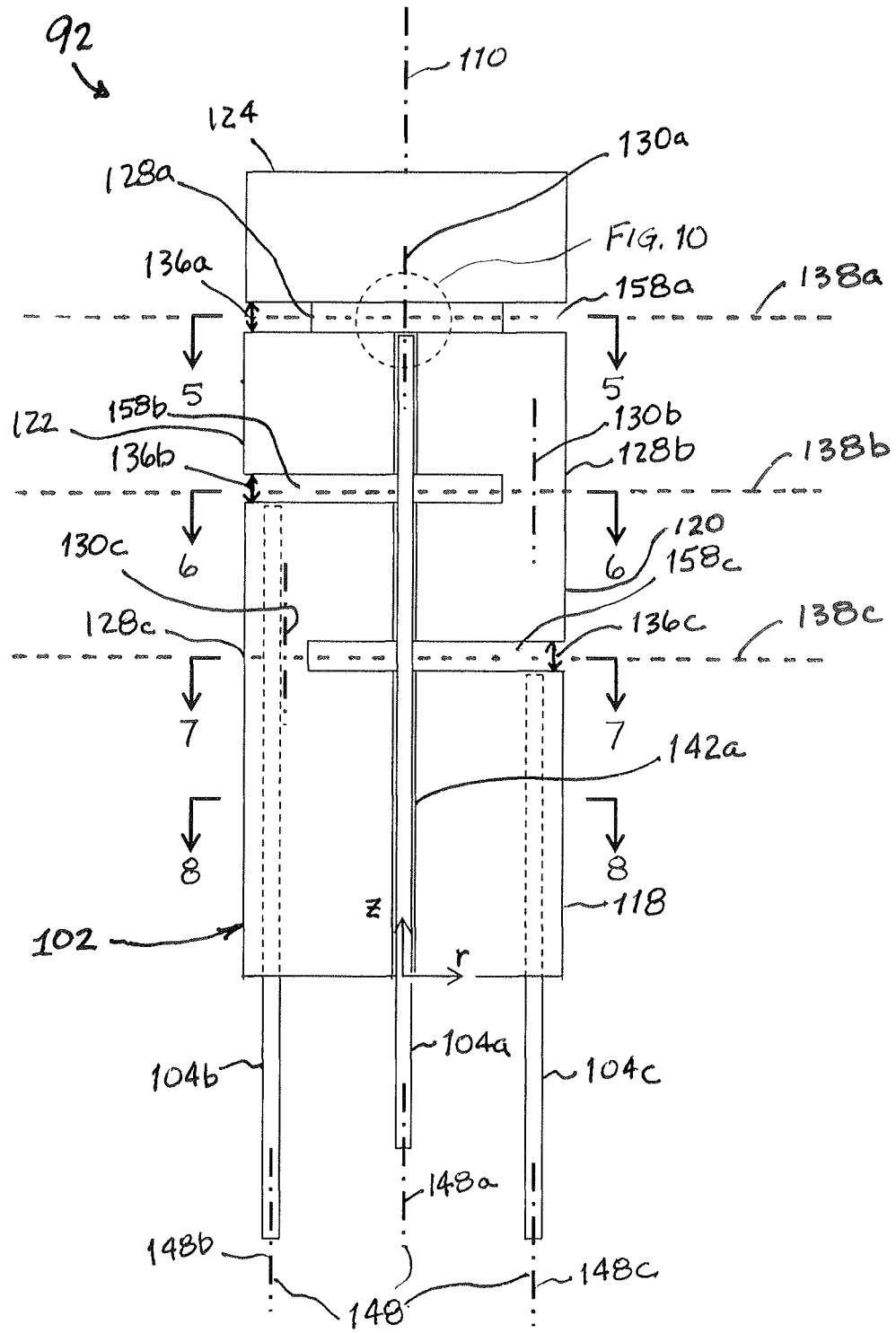
FIG. 4 is an elevation view of the fiber optic force sensing assembly of FIG. 3.

Referring to FIG. 2, an example of the end effector 88 comprising an ablation head 88a and including a fiber optic force sensing assembly 92 is depicted in an embodiment of the invention. The fiber optic force sensing assembly 92 may be configured to structural deformations in a structural member 102 caused by a force F imposed on a distal extremity 94 of the catheter, e.g., when distal extremity 94 contacts the wall of a bodily vessel or organ.

It is understood that one or more end effectors 88 of different kinds, e.g., mapping electrodes or ablation electrodes, such as are known in the art for diagnosis or treatment of a vessel or organ may be utilized with the invention. For example, the catheter assembly 87 may be configured as an electrophysiology catheter for performing cardiac mapping and ablation. In other embodiments, the catheter assembly 87 may be configured to deliver drugs or bioactive agents to a vessel or organ wall or to perform minimally invasive procedures such as transmyocardial revascularization or cryo-ablation.

Referring to FIGS. 3 through 10, the fiber optic force sensing assembly 92 including the structural member 102 and a plurality of fiber optics 104 is depicted in an embodiment of the invention. In this embodiment, the structural member 102 defines a longitudinal axis 110 and includes an outer surface 112. The structural member 102 is divided into a plurality of segments 116, identified in FIGS. 3 through 10 as a base segment 118, a proximal segment 120, a middle segment 122 and a distal segment 124. The segments 116 may be adjacent each other in a serial arrangement along the longitudinal axis 110.

The segments 116 may be bridged by a plurality of flexure portions 128, identified individually as flexure portions 128*a*, 128*b* and 128*c*, thus defining a plurality of neutral axes 130, identified individually as neutral axes 130*a*, 130*b* and 130*c*. Each neutral axis 130 constitutes the location within the respective flexure portion 128 that the stress is zero when subject to pure bending in any direction.

In one embodiment, adjacent members of the segments 116 may define a plurality of gaps 136, each having a separation dimension. For clarity, the gaps 136 are identified as 136*a* through 136*c*. The separation dimensions of the gaps 136*a*, 136*b* and 136*c* may be of the same approximate magnitude (as depicted) or of different magnitudes (not depicted). It is further noted that while the separation dimensions of the gaps 136 are depicted as being uniform, the separation dimension may vary in the lateral direction across a given gap 136*a*, 136*b*, 136*c*. Each gap 136*a*, 136*b* and 136*c*, whether of a uniform or a non-uniform separation dimension, may define a corresponding central plane 138*a*, 138*b* and 138*c* located equidistant between adjacent ones of the segments 116.

The structural member 102 may include a plurality of grooves 142 (identified in FIGS. 3 through 10 as grooves 142*a*, 142*b* and 142*c*) that are formed on the outer surface 112. The grooves 142 may be spaced rotationally equidistant (i.e. spaced 120° apart) about the longitudinal axis 110 and may be oriented in a substantially axial direction along the structural member 102. Each of the grooves may terminate at a respective one of the gaps 136. For example, the groove 142*a* may extend along the base segment 118, the proximal segment 120 and the middle segment 122, terminating at the gap 136*a*. Likewise, groove 142*b* may extend along the base segment 118 and the proximal segment 120, terminating at the gap 136*b*. And groove 142*c* may extend along the base segment 118, terminating at the gap 136*c*.

The fiber optics 104 (identified in FIGS. 3 through 10 as fiber optics 104*a*, 104*b* and 104*c*) define a plurality of light propagation axes 148 and distal ends 150 (identified in FIGS. 3 through 10 as distal ends 148*a* through 148*c* and 150*a* through 150*c*, respectively). The fiber optics 104 may be disposed in the grooves 142 (identified in FIGS. 3 through 10 as 142*a*, 142*b* and 142*c*) such that the distal ends 150 terminate at the gaps 136. For example, the fiber optic 104*a* may extend along the groove 142*a*, terminating proximate or within the gap 136*a*. Likewise, fiber optics 104*b* and 104*c* may extend along the grooves 142*b* and 142*c*, respectively, terminating proximate or within the gaps 136*b* and 136*c*, respectively.

Figure 9:
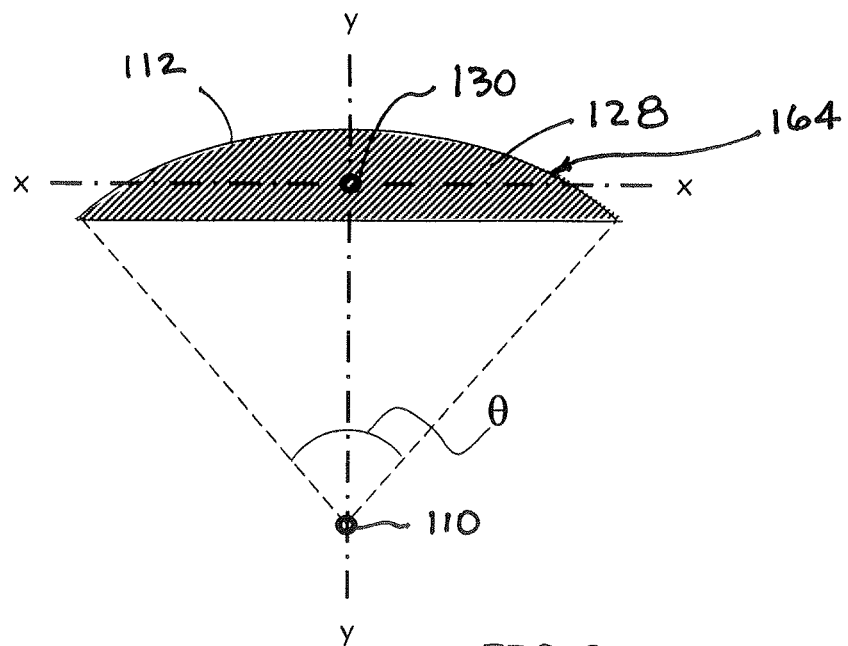
FIG. 9 is an enlarged sectional view of a flexure defining a circular segment in an embodiment of the invention.

By the above described arrangement, each of the light propagation axes 148 of the fiber optics 104 are subtended by a respective one of the segments 116. For example, as depicted in FIG. 9, the light propagation axis 148*a* is subtended by a surface 154*a* of the distal segment 124, which defines the boundary of the gap 136*a* opposite the distal end 150*a*. Accordingly, the surfaces 154 of the segments 116 that are proximate the subtended light propagation axes 148 may be made highly reflective.

Figure 5:
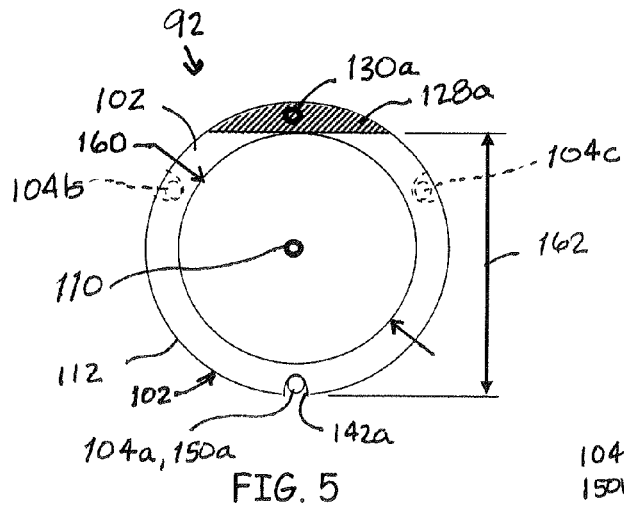
FIGS. 5 through 8 are sectional views of the fiber optic force sensing assembly of FIG. 4.
Figure 6:
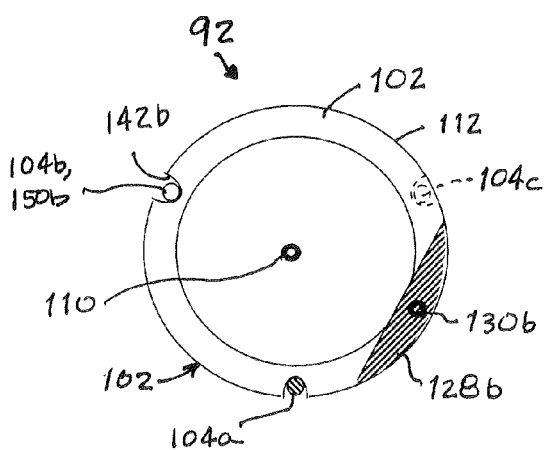
Figure 7:
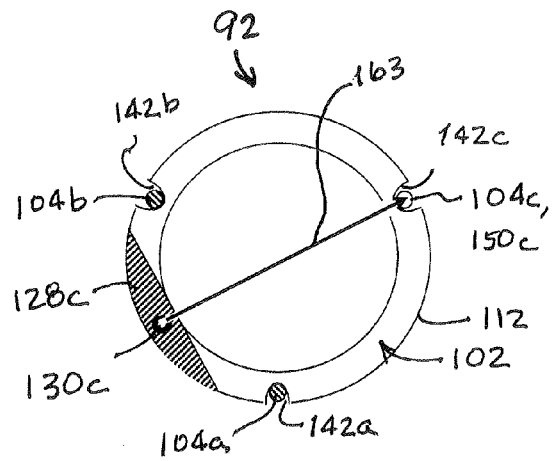
Figure 8:
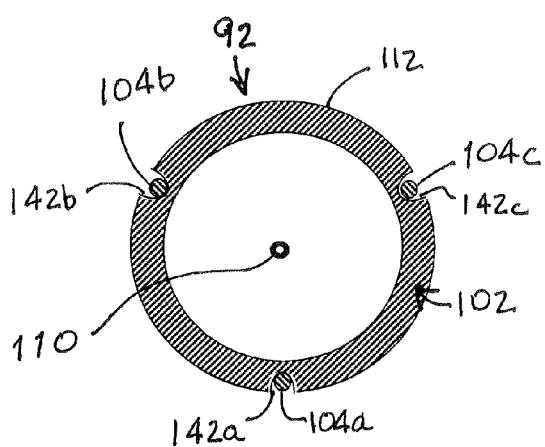

The gaps 136 may be formed so that they extend laterally through a major portion of the structural member 102. Also, the gaps 136 may be oriented to extend substantially normal to the longitudinal axis 110 (as depicted) or at an acute angle with respect to the longitudinal axis. In the depicted embodiment, the structural member comprises a hollow cylindrical tube 156 with the gaps 136 comprising slots 158 that are formed from one side of the hollow cylindrical tube 156 and are transverse to the longitudinal axis 110, extending through the longitudinal axis 110 and across the inner diameter 160 of the hollow cylindrical tube 156 to a depth 162 (FIG. 5).

By this process, the flexure portions 128 remain, defining a circular segment. The depth 162 of the slots 158 traverse the inner diameter 160 of the hollow cylindrical tube 156 can be varied to establish a desired flexibility of the flexure. That is, the greater the depth 162 the more flexible the flexure portion 128. The slots 156 may be formed by the various ways available to the artisan, such as but not limited to sawing, laser cutting or electro-discharge machining (EDM).

The slots 158 may be formed so that the flexure portions 128 define non-coincident neutral axes 130. That is, neutral axis 130*a* is located at a circumferential position about the longitudinal axis 110 that substantially differs from the circumferential position of the neutral axes 130*b* and 130*c*. The neutral axes 130 may be, but need not be, diametrically opposed to the location of the distal end 150 of the fiber optic 104 that terminates in the same gap 136 as is bridged by the respective flexure portion 128. For example, flexure portion 128*a* may be diametrically opposed to distal end 150*a*, and so on.

A cross-section 164 of the flexure portions 128 is depicted in FIG. 9. The cross-section is characterized by an area centroid C that corresponds with the neutral axis 130, and as having inertial axes x-x and y-y that are orthogonal, and where the inertial axis x-x identifies the axis about which the area moment of inertia is minimum. The circular segment geometry provides substantially greater stiffness about inertial axis y-y than about inertial axis x-x. Consider a circular segment having an angle of π/2 radians (90°). The area moment of inertia about the inertial axis y-y is about twenty times greater than the area moment of inertia about the inertial axis x-x. Accordingly, forces that cause a moment about inertial axis y-y will typically cause very little bending relative to the same moment being applied about inertial axis x-x. Therefore, moments about inertial axis y-y will tend to be transferred as a torsional force between adjacent sections, whereas moments about inertial axis x-x will tend to cause a deflection.

A deflection beam length 163 is defined as the distance between the neutral axis 130 and the center of the distal end 150 of the corresponding fiber optic 104, the distance being normal to the inertial axis x-x. By locating the distal end 150 and the neutral axis 130 of a given gap 136 in diametric opposition, the deflection beam length 163 is maximized, and so is the attendant change in the dimension of the gap proximate the distal end 150.

In one embodiment, each gap 136 enables an interferometric gap 166 to be defined between the distal end 150 of the respective fiber optic 104 and the high reflective surface 154. An "interferometric gap" as used herein is a gap having the attributes an interferometric resonator, such as found in a Michelson interferometer or a Fabry-Perot resonator. Likewise, a "gap interferometer" as used herein is an interferometer that utilizes an interferometric gap to produce an interference pattern.

The interferometric gap 166 may be characterized as having an operative length 167, defined as the distance between the distal end 150 and the high reflective surface 154 and which may differ from the dimension of the respective gap 136. The operative length 167 establishes the characteristics of the interference pattern reflected back from the interferometric gap 166. The distal ends 150 may be faced with a semi-reflecting surface or coating 168 that re-reflects a portion of the light reflected from the high reflective surface 154 while substantially transmitting the remaining portion of the reflected light therethrough for detection by the strain sensing system 70.

In another embodiment, light is transmitted and reflected back across the respective gaps 136, with the reflected light being collected by the distal end 150 of the respective fiber optic 104. The intensity of the reflected light collected by a given fiber optic 104 may vary with the distance between the distal end 150 and the high reflective surface 154. Embodiments that utilize the variation of reflected light intensity may utilize distal ends 150 that are exposed rather than face with the semi-reflecting surface or coating 168, thereby increasing the amount of light that can be detected.

In one embodiment, the fiber optics 104 are bonded to the structural member 102 with an adhesive or bonding material 170. Alternatively or in addition, the fiber optics 104 may be press fit or otherwise fastened to the structural member 102. For configurations that employ an intensity or interferometric measurement, the fiber optic 104 may be bonded to the segment 116 adjacent the respective gap 136 to be interrogated. For example, fiber optic 104b may be mounted within the portion of groove 142b that is formed on the middle segment 122. The remainder of the fiber optic 104b may be left to slide freely within the remainder of the groove 142b. By this arrangement, the fiber optic 104b will not form a structural bridge between adjacent segments, which would inhibit the flexibility of the fiber optic force sensing assembly 92.

Figure 11A:
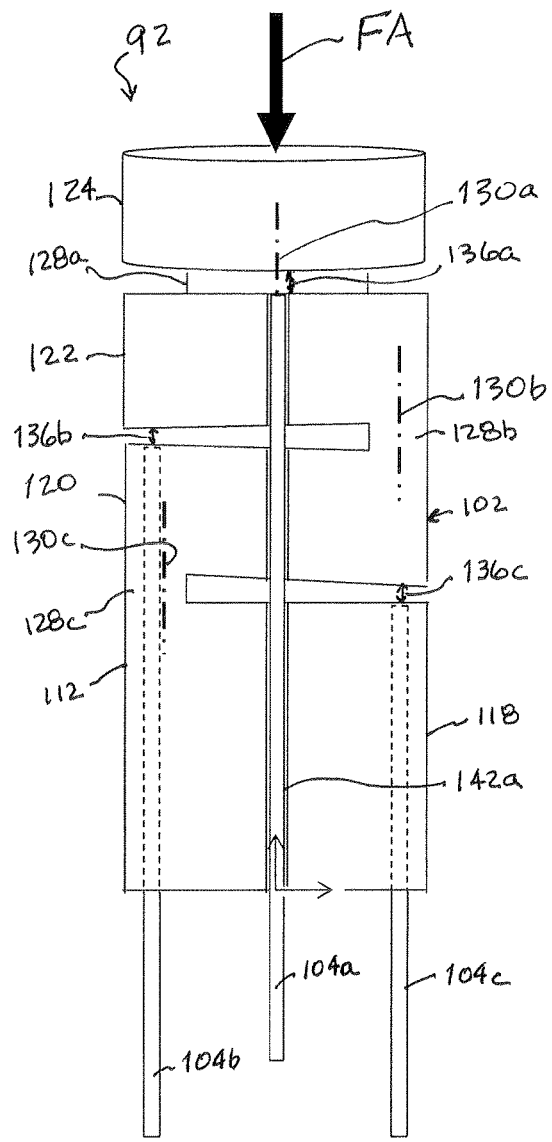
FIGS. 11A and 11B depict the deflection of the fiber optic force sensing assembly of FIG. 3 under an axial load and a lateral load, respectively.
Figure 11B:
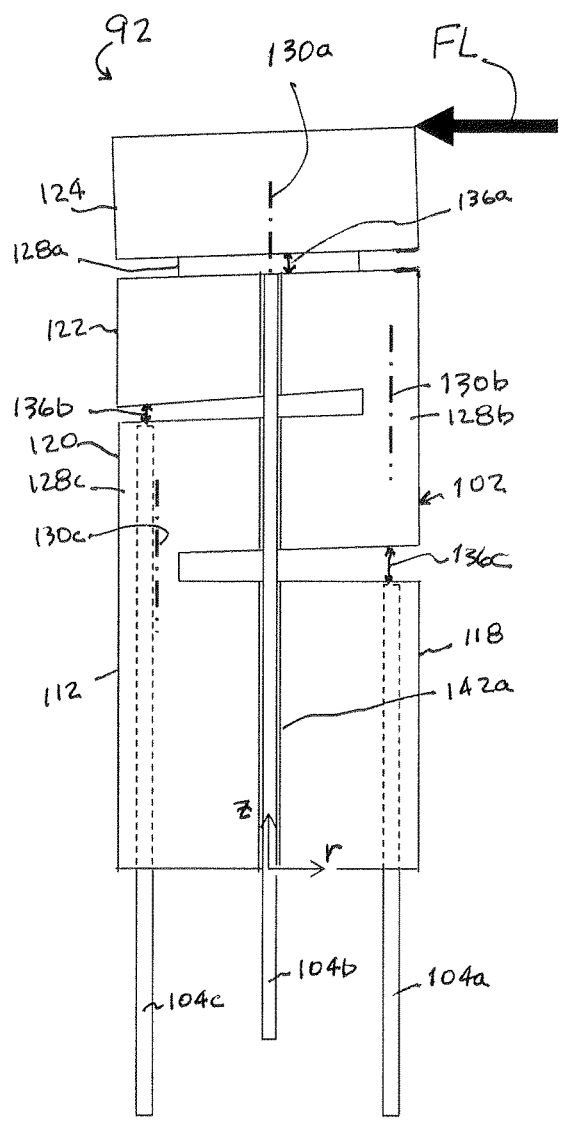
Figure 13:
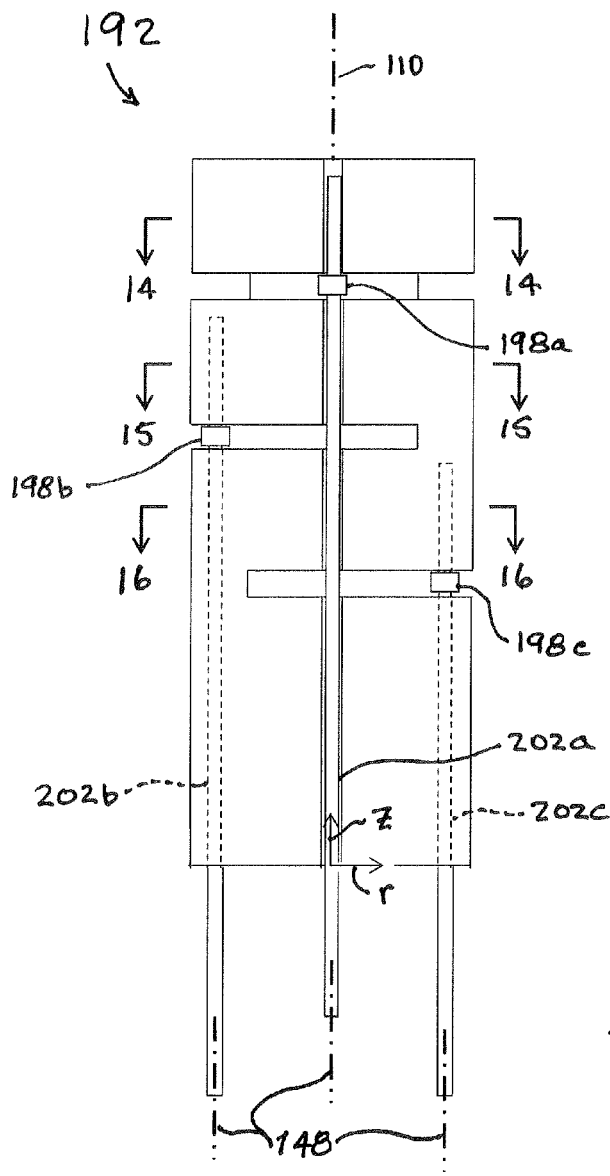
FIG. 13 is an elevation view of the fiber optic force sensing assembly of FIG. 12.

Referring to FIGS. 11A and 11B, operation of the fiber optic force sensing assembly 92 in response to an axial force FA and a lateral force FL, respectively, is depicted in an embodiment of the invention. The axial force FA causes the segments 116 to bend about the inertial axes x-x of the various flexure portions 128 in substantially a pure bending action, thus causing the dimension of the gaps 136 proximate the distal ends 150 of the fiber optics 104 to decrease (FIG. 11A). This, in turn, causes the operative lengths 167 of the interferometric gaps 166 to decrease, thereby causing a change in the frequencies of the interferometric patterns sustained across the interferometric gaps 166.

The lateral force FL will generally cause a more complex deformation of the structural member 102. In the depiction of FIG. 10B, the lateral force FL is applied substantially parallel to the inertial axis y-y of flexure portion 128a. This causes flexure portion 128a to translate a moment between distal segment 124 and middle segment 122 while causing a negligible change in the dimension of gap 136a. The translated moment causes flexure portions 128b and 128c to bend about their respective inertial axes x-x, which in turn causes the gap 136b to close proximate distal end 150b of fiber optic 104b and the gap 136c to open proximate the distal end 150c of fiber optic 104c. It is noted that in the depiction of FIG. 11B, neither flexure portion 128b or 128c are in pure bending because lateral force FL does not act normal to the respective inertial axes x-x. Hence, the degree of bending about the inertial axes x-x will generally be proportional to the component of the lateral force FL that acts normal thereto.

It is understood that FIGS. 11A and 11B show a purely axial and a purely lateral force, respectively, but that a combined force vector in three-dimensional space having an axial and a lateral component will combine the general effects depicted by superposition. Accordingly, a force vector in three-dimensional space can be resolved by calibrating the response of the fiber optic force sensing assembly under these pure loads and superimposing the various responses to infer the axial and lateral components.

The characteristics of the modulated waveform 89a (FIG. 1A) are determined in part by the dimension of the interferometric gap 85. The fiber optic force sensing assembly 92 is configured so that the interferometric gap 85 will vary when the structural member 102 experiences an axial strain. A change in the axial strain will cause a proportional change in the dimension of the interferometric gap 85, thereby altering the characteristic of the modulated waveform 89a transmitted to the receiver 76.

The preceding embodiments can provide a mechanical amplification of the change in the interferometric gap 85 relative to the strain experienced by the flexure portions 128. The deflection of the segments 116 at a position normal to the inertial axis x-x of a respective one of the flexure portions 128 is proportional to the deflection beam length 163 between the neutral axis 130 and the respective location of the distal end 150 of the respective fiber optic 104. Accordingly, change in the dimension of the gap 136 will be greatest at a location that is diametrically opposed to the neutral axis 130. Accordingly, for embodiments where the distal ends 150 of the fiber optics 104 in diametric opposition to the neutral axes 130 (as depicted herein), the fiber optics 104 are in a position of greatest sensitivity.

The structural member 102 may be fabricated from other forms besides a hollow cylindrical tube, including but not limited to tubes or rods that define a square, rectangular or cross-shaped cross-section. The structural member 102 may comprise a metallic material, such as titanium or platinum/iridium, or a non-metallic material such as a polymer or ceramic. The gaps 136 and flexure portions 128 may be sized so that the change in the operative lengths 167 due to application of forces FA and FL is of substantially higher sensitivity than the change caused thermal expansion or contraction of the structural member 102 under operation.

Furthermore, the material for structural member 102 may be selected to mitigate against the effects of thermal expansion. For example, the structural member 102 may be constructed of a material having a low coefficient of thermal expansion, such as fused quartz, aluminum oxides such as alumina ($Al_2O_3$), liquid crystal polymer, or from metal/ceramic composites such as Invar designed to for a low coefficient of thermal expansion relative to metals.

The adhesive or bonding material 170 may comprise a glue or epoxy. The bonding material 170 may be selected to closely match the coefficient of thermal expansion (CTE) of the structural member 102 and/or fiber optics 104, or to provide a CTE that is between the CTEs of the structural member 102 and fiber optics 104 to provide a transition therebetween. The bonding material 170 may also be chosen for flexibility so that the thermal growth of the adhesive film does not impose a substantial strain on the fiber optics 104. Use of a very thin film of bonding material 170 may, in some instances, mitigate the effects of differential thermal expansion.

Where the structural member 102 comprises a polymer material, the fiber optics 104 may be bonded directly to the polymer using a bonding technique that involves the use of a solvent designed to cause the polymer to melt or flow while not affecting the material of the fiber optics 104. The solvent may be applied to an area or zone of the structural member 102 where the fiber optics 104 are to be mounted, and the fiber optics 104 placed thereon. Alternatively, the fiber optics 104 may be temporarily held in place on the zone or area of the structural member 102 and the solvent applied to both. The flowing of the material causes a bond between the structural member 102 and the outer surface of the fiber optics 104. The solvent may be removed by a process such as washing or evaporation to arrest the melting process.

The reflective surfaces 154 may be fabricated by polishing a metallic structural member 102, or by depositing a reflective material on either of a metallic or a non-metallic structural member 102. Representative and non-limiting dimensions for the structural member are approximately 1- to 10-mm in length, approximately 0.3- to 3-mm in diameter, and gap dimensions of approximately 15- to 100-micorometers.

Referring to FIGS. 12, 12A and FIGS. 13 through 16, a fiber optic force sensing assembly 192 including a structural member 196 is depicted in an embodiment of the invention. The structural member 196 includes many of the same aspects as the structural member 102 of FIGS. 3 through 9, which are labeled in the respective figures with the same numerical references. The fiber optic force sensing assembly 192 includes fiber optics 202 (identified in FIGS. 12 through 16 as fiber optics 202a, 202b and 202c) each operatively coupled to a respective one of a plurality of Fabry-Perot strain sensors 198 (identified as 198a, 198b and 198c). Fabry-Perot strain sensors of the general configuration presented in FIG. 12A are commercially available from FISO Technologies of Quebec, QC, Canada.

The operation of the Fabry-Perot strain sensors 198 is depicted in FIG. 12A. The fiber optic 202 is split into a transmitting element 204a and a reflecting element 204b, each being anchored at opposing ends of a hollow tube 206. The transmitting and reflecting elements 204a and 204b are positioned to define an interferometric gap 205 therebetween having an operative length 207. The free end of the transmitting element 204a may be faced with a semi-reflecting surface 200a, and the free end of the reflecting element 204b may be faced with a reflecting surface 200b.

The fiber optics 202 may be positioned along the grooves 142 so that the respective Fabry-Perot strain sensor 198 is bridged between by the respective fiber optic 202 and across segments 116 that are adjacent each other. For example, fiber optic 202a may be positioned within groove 142a so that the Fabry-Perot strain sensor 198a bridges the gap 136a between the middle segment 122 and the distal segment 124. Likewise, fiber optics 202b and 202c may be positioned so that Fabry-Perot sensors 198b and 198c to bridge the gaps 136b and 136c, respectively.

Figure 14:
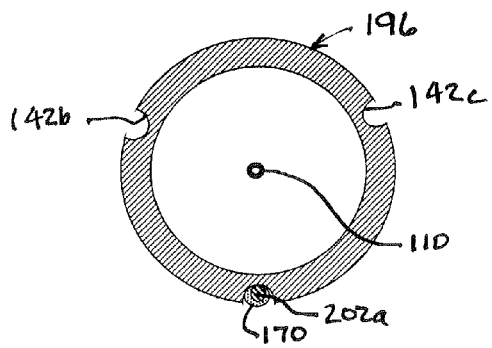
FIGS. 14 through 16 are sectional views of the fiber optic force sensing assembly of FIG. 13.
Figure 15:
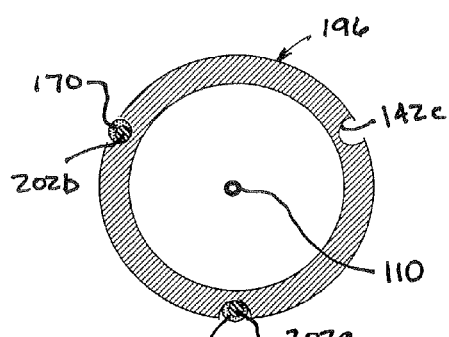
Figure 16:
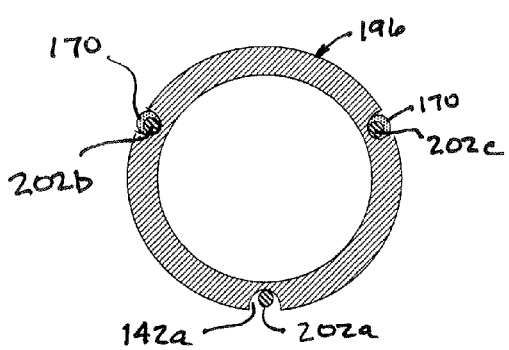
Figure 17:
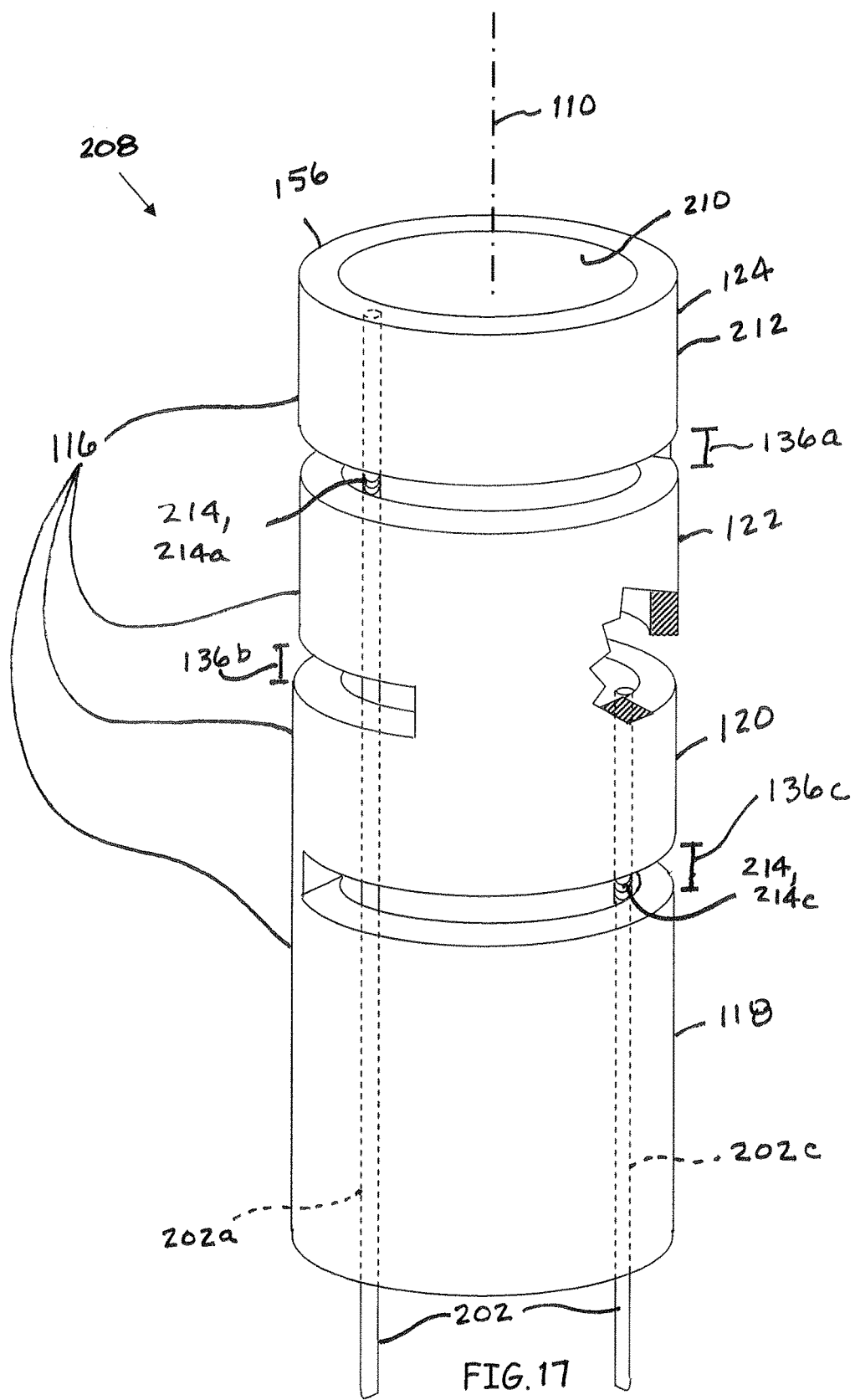
FIG. 17 is an enlarged perspective partial cutaway view of a second fiber optic force sensing assembly that utilizes a fiber Bragg grating strain sensor in an embodiment of the invention.
Figure 18:
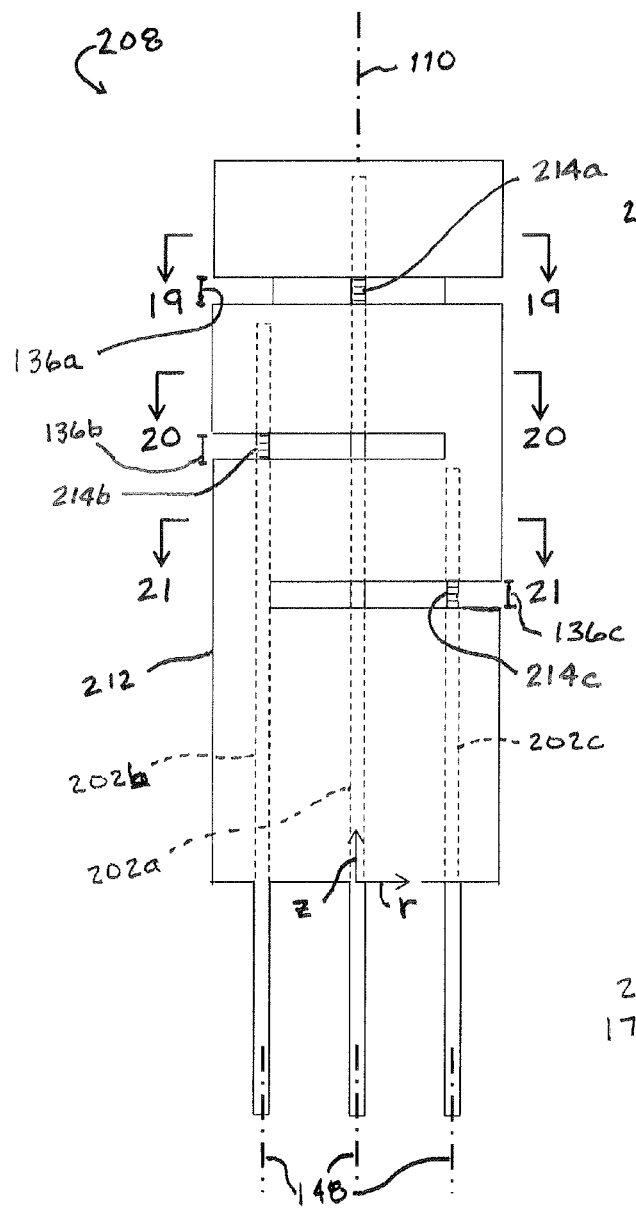
FIG. 18 is an elevation view of the fiber optic force sensing assembly of FIG. 17.
Figure 19:
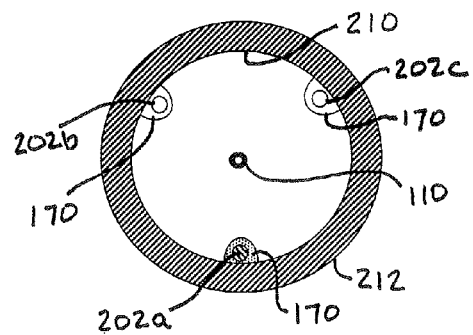
FIGS. 19 through 21 are sectional views of the fiber optic force sensing assembly of FIG. 18.
Figure 20:
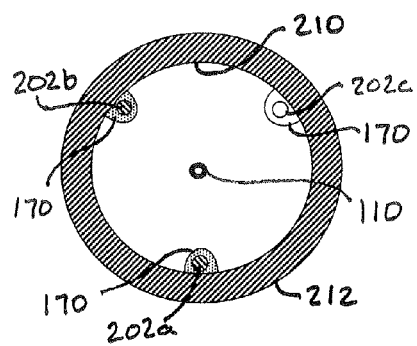
Figure 21:
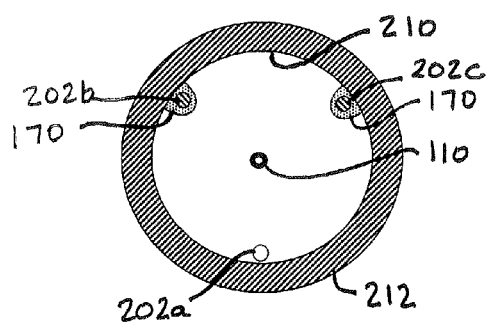

The fiber optic 202 may be operatively coupled to both the adjacent segments 116 that the fiber optic 202 bridges. The fiber optics 202 may be attached using the adhesive or bonding material 170 to the segments 116, as best seen in FIGS. 14 through 16. In this embodiment, the bonding material 170 is applied only to the segments 116 that are adjacent the gap 136 bridged by the fiber optic 202. For example, fiber optic 202a is attached only to the middle and distal segments 122 and 124 (FIGS. 14 and 15), but not to the proximal segment 120 (FIG. 16) or the base segment 118. The grooves 142 may also extend the full length of the structural member 196, as depicted in FIG. 12, as there is no need for the structural member 196 to reflect light back into the fiber optics 202.

Referring to FIGS. 17 through 21, a fiber optic force sensing assembly 208 is depicted in an embodiment of the invention. The fiber optic force sensing assembly 208 utilizes fiber optics 202 having a fiber Bragg grating strain sensor 214. In this embodiment, the fiber optics 202 are disposed on an interior surface 210 of a structural member 212. Accordingly, the structural member 212 need not include grooves that run axially on the exterior surface. Otherwise, the fiber optics 202 are aligned along the length of the structural member 212 and attached to the interior surface 210 so that the fiber Bragg grating strain sensors 214 fixedly bridge adjacent segments 116. Again, the fiber optics 202 may be affixed to the interior surface 212 using the bonding material 170.

In operation, when a force is applied at or near the distal extremity 94 of either of the structural members 196 or 212, the structural member 196, 212 will have a tendency to flex, for example, as depicted in FIGS. 11A and 11B. However, the fiber optics 202 being fixedly attached to adjacent segments 116 causes a restorative or reactive force that limits deflection between the segments 116 of the structural member 196. The reactive forces, which may be a compressive force or a tension force, causes a strain across the strain sensors of the fiber optics 202 (Fabry-Perot strain sensors 198 of the fiber optic force sensing assembly 192 or fiber Bragg grating strain sensors 214 of the fiber optic force sensing assembly 208).

The fiber optic force sensing assembly 192 may be configured so that the axial force and strain exerted on the fiber optics 202 is at a desired level. For example, the diameter of the fiber optics 202 will have an effect on the strain imposed on the fiber Bragg grating strain sensor 214, with smaller diameter fiber optics providing a greater strain per unit of axial force. Also, the geometry of the flexure portions 128 will affect the magnitude of the force that is transferred to the fiber optics 202. That is, a flexure portion 128 having a greater stiffness (i.e. a greater area moment of inertia about the inertial axis x-x) will transfer less force to the respective fiber optic 202. Moreover, the magnitude of the reactive force will vary with the normal distance between the fiber optic 202 and the inertial axis x-x, with the reactive force generally increasing as the normal distance decreases. Hence, the reactive force for a single fiber optic located at the deflection beam length 163 (FIG. 7) will be less than for a single fiber optic located on the structural element 102 that defines a normal distance between the optic 202 and the inertial axis x-x that is shorter than the deflection beam length 163.

By tweaking these various parameters, the strain sensed by a fiber optic strain sensor may be tailored to provide a desired sensitivity. In terms of the reactive forces, it is contemplated that the ratio of the flexure axial force to the fiber optic axial force can range from 0.2 to 5.

It is noted that while the depicted embodiments present a single fiber optic diametrically opposed to the neutral axis of a respective flexure (e.g., fiber optic 202a in diametric opposition to neutral axis 130a), the invention is not so limited. The fiber optics of the various embodiments may be located on the structural body at a location other than diametric opposition with respect to the neutral axis of a given flexure. Moreover, the number of fiber optics utilized for detecting the forces exerted may be greater than one. For example, a configuration utilizing a fiber optic strain sensor (e.g., fiber Bragg grating strain sensors 214) may include a pair of fiber optic strain sensors, each located at a circumferential location on the structural member that defines restorative moment arms about the inertial axis x-x that are of equal magnitude. It is further noted that the Fabry-Perot detection schemes and the fiber Bragg grating detection schemes may each be present on the same fiber optic force sensing assembly.

For the fiber optic force sensing assembly 208, the strain causes the interferometric gap of the Fabry-Perot strain sensor 198 to change and the frequency of the returned modulated waveform to shift in frequency. The frequency change can be calibrated to correspond to the reactive force using known techniques. For the fiber optic force sensing assembly 208, the strain causes a shift in the central wavelength of the light that is reflected by the respective fiber Bragg grating strain sensor 214, which can be calibrated to correspond to the reactive force using known techniques.

The invention may be practiced in other embodiments not disclosed herein, such as endoscopic or additional intravascular applications. For example, various aspects of the disclosed embodiments may be utilized in a diagnostic catheter for optimizing or otherwise improving the placement of excitation electrodes for baroreflex activation. Other aspects of the disclosed embodiments may find application in endoscopic applications, such as orthoscopic surgery or entry through open orifices such as the throat, nose or anus without departing from the spirit of the invention.

References to relative terms such as upper and lower, front and back, left and right, or the like, are intended for convenience of description and are not contemplated to limit the invention, or its components, to any specific orientation. All dimensions depicted in the figures may vary with a potential design and the intended use of a specific embodiment of this invention without departing from the scope thereof.

Each of the additional figures and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "step for" are recited in the subject claim.

The invention claimed is:

1. A method, comprising:
providing a catheter to a user, the catheter configured for exploration or treatment of a vessel, organ or other tissue, said catheter comprising:
a flexible elongated body having a proximal end and a distal extremity; and
a fiber optic force sensing assembly disposed within said flexible elongated body proximate said distal extremity, said fiber optic force sensing assembly including:
a structural member having an outer surface and defining a longitudinal axis,
said structural member including a plurality of segments that are adjacent each other in a serial arrangement along said longitudinal axis to define a plurality of gaps, each of said plurality of gaps being located between adjacent ones of said plurality of segments;
a plurality of flexures dispersed between said plurality of segments so that said adjacent ones of said plurality of segments are bridged by one of said plurality of flexures, each of said flexures defining a portion of said outer surface of said structural member; and
a plurality of fiber optics operatively coupled with said structural member; and
providing instructions recorded on a tangible medium to the user, the instructions for utilizing the catheter to determine one or more contact forces between the distal extremity of the catheter and the vessel, organ or other tissue, the instructions comprising:
manipulating the catheter such that at least the distal extremity contacts the vessel, organ or other tissue, to cause the distal extremity of the catheter to deflect in response to the contact;
computing a multi-dimensional contact force vector from an output signal from the fiber optic force sensing assembly and
providing an indication to the user based on the multi-dimensional contact force vector.

2. The method of claim 1, wherein each of said plurality of fiber optics includes a distal end disposed adjacent one of said plurality of gaps and oriented for emission of light onto and for collection of light reflected from the segment adjacent said one of said plurality of gaps, wherein a distance between said distal and of said fiber optic and said segment adjacent said one of said plurality of gaps and opposite said distal end of said fiber optic has a dimension that changes in response to bending of a one of said flexures that bridges said one of said plurality of gaps, and further wherein the multi-dimensional contact three vector is computed at least in part based on the change in the dimension.

3. The method of claim 2, wherein said distal end of said fiber optic and said segment adjacent said one of said plurality of gaps defines an interferometric gap.

4. The method of claim 2, wherein said collection of light reflected from the segment adjacent said one of said plurality of gaps varies in intensity in response to bending of said one of said flexures that bridges said one of said plurality of gaps.

5. The method of claim 2, wherein said distal end of said fiber optic is diametrically opposed to the corresponding flexure that bridges said one of said plurality of gaps.

6. The method of claim 1, the instructions further comprising: measuring an electrical potential of the vessel, organ or other tissue if the contact force is within a predetermined range.

7. The method of claim 1, wherein the catheter further comprises a treatment end effector coupled to the elongated body distal to the fiber optic force sensing assembly, the instructions further comprising: controlling operation of the treatment end effector based on the computed contact force.

8. The method of claim 7, wherein controlling operation of a treatment end effector comprises positioning the end effector in contact with the vessel, organ or other tissue and energizing an ablation electrode if the contact force is within a predetermined range.

9. A method, comprising:
providing a fiber optic force sensing assembly to a user, the assembly comprising:
a structural member defining a longitudinal axis and including a plurality of segments
that are adjacent each other in a serial arrangement along said longitudinal axis, each of adjacent ones of said plurality of segments defining a gap therebetween, each gap being bridged by a flexure; and
a plurality of fiber optics operatively coupled with said structural member, wherein said
flexure defines a cross-section on a plane orthogonal to said longitudinal axis, said cross-section defining an area centroid, a first inertial axis and a second inertial axis being defined as passing through said area centroid, said second inertial axis being normal to said first inertial axis and intersecting said longitudinal axis of said structural member, the area moment of inertia about said second inertial axis being at least ten times greater than the area moment of inertia about said first inertial axis; and providing instructions recorded on a tangible medium to the user, the instructions for utilizing the assembly to determine one or more contact forces between a distal extremity of the structural member and a vessel, organ or other tissue, the instructions comprising:

manipulating the structural member such that at least the distal extremity contacts the vessel, organ or other tissue, to cause the distal extremity of the catheter to deflect in response to the contact;

computing a multi-dimensional three vector from an output signal from the fiber optic force sensing assembly; and providing an indication to the user based on the multi-dimensional force vector.

10. The method of claim 9, wherein the area moment of inertia about said first inertial axis of the fiber optic force sensing assembly is the minimum area moment of inertia of said cross-section of said flexure.

11. The method of claim 9, wherein the plurality of fiber optics of the fiber optic force sensing assembly cooperate with said structural member to define a plurality of interferometric gaps.

12. The method of claim 9, wherein each of said plurality of fiber optics of the fiber optic force sensing assembly include one of a Fabry-Perot resonator and a fiber Bragg grating.

13. The method of claim 12, wherein said Fabry-Perot resonator comprises an intrinsic Fabry-Perot interferometer.

14. The method of claim 9, wherein the cross-section of said flexure of the fiber optic force sensing assembly defines a circular segment.

15. The method of claim 9, wherein said plurality of segments of the fiber optic three sensing assembly define a plurality of said gaps and a plurality of said flexures, said flexures being distributed about said longitudinal axis.

16. The method of claim 15, wherein said plurality of flexures number three, the flexures being centered at 120-degree intervals about said longitudinal axis.

* * * * *